(12) United States Patent
Ferrara

(10) Patent No.: US 8,110,720 B2
(45) Date of Patent: Feb. 7, 2012

(54) TRANSGENIC MICE EXPRESSING HUMANIZED VEGF

(75) Inventor: Napoleone Ferrara, San Francisco, CA (US)

(73) Assignee: Genentech, Inc, South San Francisco, CA (US)

( * ) Notice: Subject to any disclaimer, the term of this patent is extended or adjusted under 35 U.S.C. 154(b) by 0 days.

(21) Appl. No.: 12/520,844

(22) PCT Filed: Dec. 21, 2007

(86) PCT No.: PCT/US2007/088537
§ 371 (c)(1),
(2), (4) Date: Feb. 1, 2010

(87) PCT Pub. No.: WO2008/080052
PCT Pub. Date: Jul. 3, 2008

(65) Prior Publication Data
US 2010/0162415 A1    Jun. 24, 2010

Related U.S. Application Data

(60) Provisional application No. 60/871,736, filed on Dec. 22, 2006.

(51) Int. Cl.
*A01K 67/027* (2006.01)
*C07H 21/02* (2006.01)
*A01K 67/00* (2006.01)
(52) U.S. Cl. ............................ 800/18; 800/8; 536/23.1
(58) Field of Classification Search .................. 800/8, 18; 536/23.1
See application file for complete search history.

(56) References Cited

U.S. PATENT DOCUMENTS

| 5,332,671 A | * | 7/1994 | Ferrara et al. | 435/360 |
| 6,130,071 A | * | 10/2000 | Alitalo et al. | 435/69.4 |
| 6,479,729 B1 | * | 11/2002 | Campochiaro et al. | 800/18 |

OTHER PUBLICATIONS

Mouse VEGF-A gene sequence printout from www.ncbi.nlm.gov/nuccore/27544278, dated Dec. 31, 2010, p. 1-3.*
Ko et al. Infection and Immunity 73(9):5666-5674, Sep. 2005.*
Naito et al. J Reprod Fert 113:137-143, 1998.*
Aiello et al., "Vascular endothelial growth factor in ocular fluid of patients with diabetic retinopathy and other retinal disorders" *New England J. of Medicine* 331(22):1480-1487 (Dec. 1, 1994).
Berkman et al., "Expression of the vascular permeability factor/vascular endothelial growth factor gene in central nervous system neoplasms" *J. Clin. Invest.* 91:153-159 (Jan. 1993).
Brown et al., "Expression of vascular permeability factor (vascular endothelial growth factor) and its receptors in adenocarcinomas of the gastrointestinal tract" *Cancer Research* 53:4727-4735 (Oct. 1, 1993).

Brown et al., "Expression of vascular permeability factor (vascular endothelial growth factor) and its receptors in breast cancer" *Human Pathology* 26(1):86-91 (1995).
Carmeliet et al., "Abnormal blood vessel development and lethality in embryos lacking a single VEGF allele" *Nature* 380:435-439 (Apr. 4, 1996).
Dvorak et al., "Vascular permeability factor/vascular endothelial growth factor, microvascular hyperpermeability, and angiogenesis" *American Journal of Pathology* 146(5):1029-1039 (May 1995).
Ellis et al., "Vascular Endothelial Growth Factor in Human Colon Cancer: Biology and Therapeutic Implications" *The Oncologist* 5 (Suppl 1):11-15 (2000).
Ferrara and Davis-Smyth, "The Biology of Vascular Endothelial Growth Factor" *Endocrine Reviews* 18(1):4-25 (1997).
Ferrara et al., "Heterozygous embryonic lethality induced by targeted inactivation of the VEGF gene" *Nature* 380:439-442 (Apr. 4, 1996).
Ferrara et al., "Vascular endothelial growth factor is essential for corpus luteum angiogenesis" *Nature Med.* 4:336-340 (1998).
Ferrara, N., "Molecular and biological properties of vascular endothelial growth factor" *J Mol Med* 77:527-543 (1999).
Gerber et al., "VEGF couples hypertrophic cartilage remodeling, ossification and angiogenesis during endochondral bone formation" *Nature Medicine* 5(6):623-628 (Jun. 1999).
Guerrin et al., "Vasculotropin/Vascular Endothelial Growth Factor Is an Autocrine Growth Factor for Human Retinal Pigment Cells Cultured In Vitro" *J. Cellular Physiology* 164:385-394 (1995).
Houck et al., "The Vascular Endothelial Growth Factor Family: Identification of a Fourth Molecular Species and Characterization of Alternative Splicing of RNA" *Mol. Endocrinol.* 5(12):1806-14 (1991).
Kerbel, "Clinical trials of antiangiogenic drugs: opportunities, problems, and assessment of initial results" *J Clin Oncol.* 19(18 Suppl):45S-51S (Sep. 2001).
Leung et al., "Vascular Endothelial Growth Factor is a Secreted Angiogenic Mitogen" *Science* 246:1306-1309 (Dec. 8, 1989).
Lopez et al., "Transdifferentiated retinal pigment epithelial cells are immunoreactive for vascular endothelial growth factor in surgically excises age-related macular degeneration-related choroidal neovascular membranes" *Invest. Ophthalmol. Vis. Sci.* 37(5):855-868 (Apr. 1996).
Mattern et al., "Association of vascular endothelial growth factor expression with intratumoral microvessel density and tumour cell proliferation in human epidermoid lung carcinoma" *Brit. J. Cancer* 73:931-934 (1996).
Oberg-Welsh et al., "Effects of vascular endothelial growth factor on pancreatic duct cell replication and the insulin production of fetal islet-like cell clusters in vitro" *Mol. Cell. Endocrinol.* 126:125-132 (1997).
Rosen, "Antiangiogenic strategies and agents in clinical trials" *Oncologist.* 5(Suppl 1):20-7 (2000).
Sondell et al., "Vascular Endothelial Growth Factor Has Neurotropic Activity and Stimulates Axonal Outgrowth, Enhancing Cell Survival and Schwann Cell Proliferation in the Peripheral Nervous System" *J. Neurosci* 19:5731-5740 (1999).

* cited by examiner

*Primary Examiner* — Marcia S Noble
(74) *Attorney, Agent, or Firm* — Grant Kalinowski

(57) ABSTRACT

The present invention generally relates to humanized VEGF and non-human transgenic animals expressing it. The transgenic animals are also useful to study VEGF-related therapies.

4 Claims, 10 Drawing Sheets

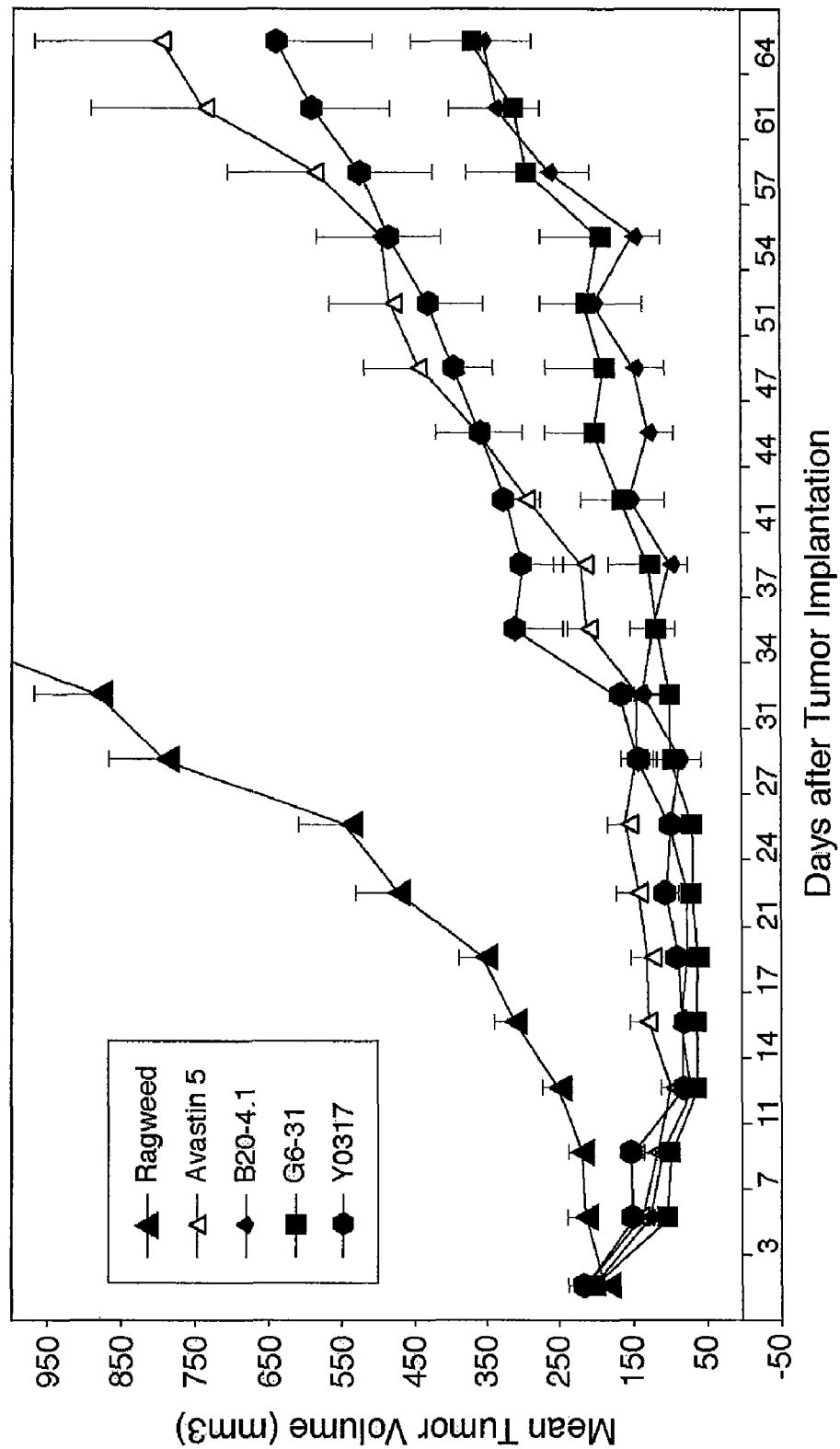

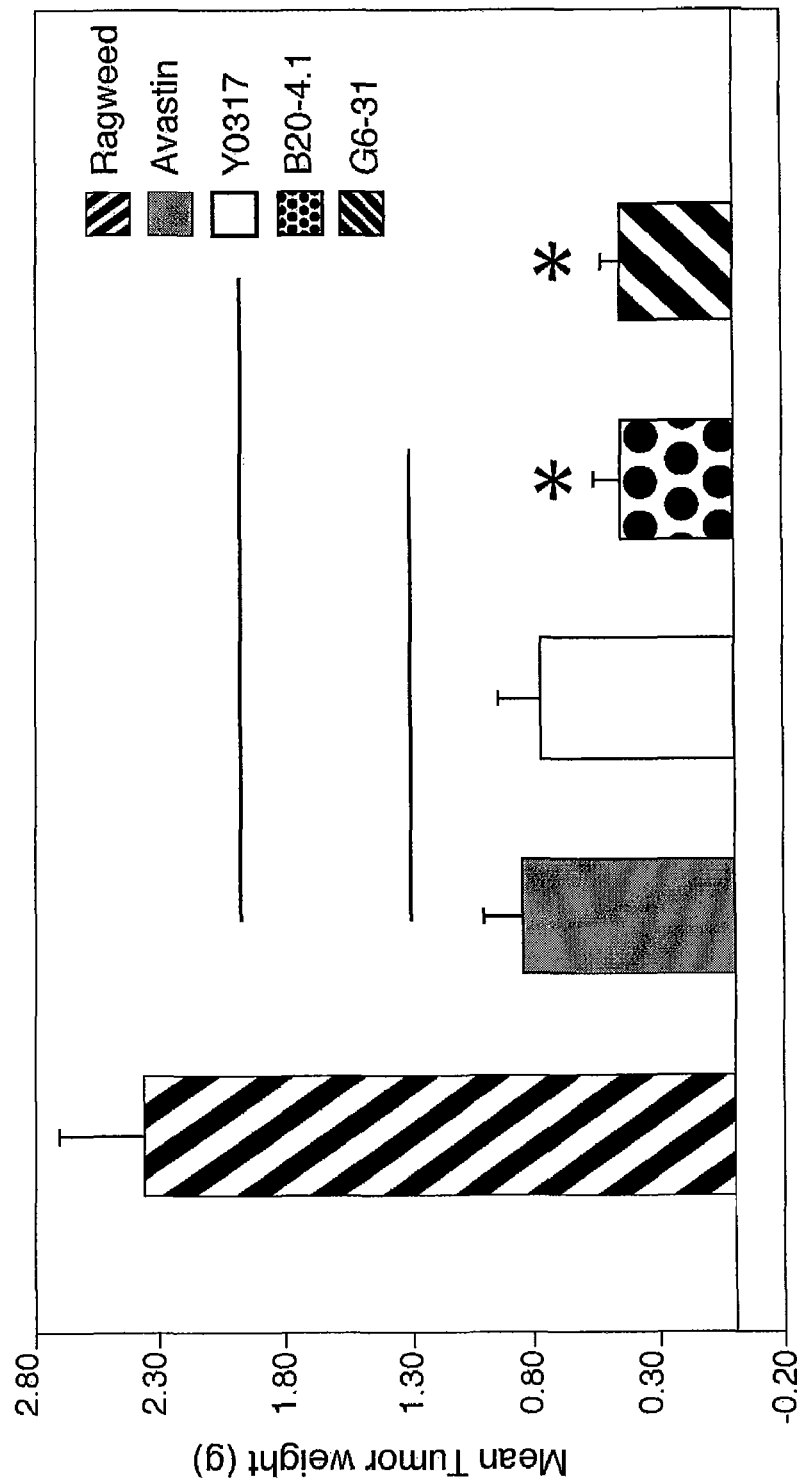

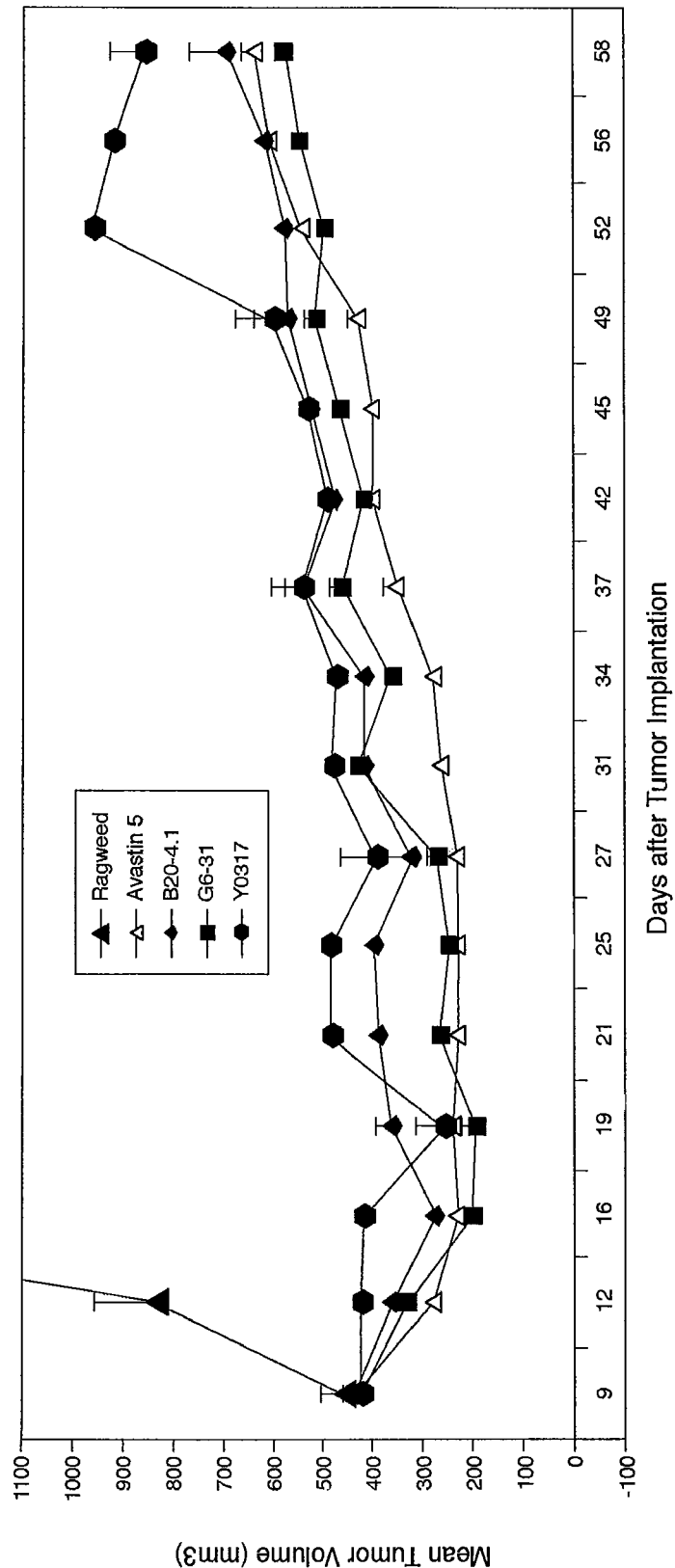

SEQUENCE LISTING

```
<160> NUMBER OF SEQ ID NOS: 12

<210> SEQ ID NO 1
<211> LENGTH: 190
<212> TYPE: PRT
<213> ORGANISM: Mus musculus

<400> SEQUENCE: 1

Met Asn Phe Leu Leu Ser Trp Val His Trp Thr Leu Ala Leu Leu
 1               5                  10                  15

Leu Tyr Leu His His Ala Lys Trp Ser Gln Ala Ala Pro Thr Thr
                20                  25                  30

Glu Gly Glu Gln Lys Ser His Glu Val Ile Lys Phe Met Asp Val
                35                  40                  45

Tyr Gln Arg Ser Tyr Cys Arg Pro Ile Glu Thr Leu Val Asp Ile
                50                  55                  60

Phe Gln Glu Tyr Pro Asp Glu Ile Glu Tyr Ile Phe Lys Pro Ser
                65                  70                  75

Cys Val Pro Leu Met Arg Cys Ala Gly Cys Cys Asn Asp Glu Ala
                80                  85                  90

Leu Glu Cys Val Pro Thr Ser Glu Ser Asn Ile Thr Met Gln Ile
                95                 100                 105

Met Arg Ile Lys Pro His Gln Ser Gln His Ile Gly Glu Met Ser
               110                 115                 120

Phe Leu Gln His Ser Arg Cys Glu Cys Arg Pro Lys Lys Asp Arg
               125                 130                 135
```

```
Thr Lys Pro Glu Asn His Cys Glu Pro Cys Ser Glu Arg Arg Lys
            140                 145                 150

His Leu Phe Val Gln Asp Pro Gln Thr Cys Lys Cys Ser Cys Lys
            155                 160                 165

Asn Thr Asp Ser Arg Cys Lys Ala Arg Gln Leu Glu Leu Asn Glu
            170                 175                 180

Arg Thr Cys Arg Cys Asp Lys Pro Arg Arg
            185                 190

<210> SEQ ID NO 2
<211> LENGTH: 191
<212> TYPE: PRT
<213> ORGANISM: Homo sapiens

<400> SEQUENCE: 2

Met Asn Phe Leu Leu Ser Trp Val His Trp Ser Leu Ala Leu Leu
  1               5                  10                  15

Leu Tyr Leu His His Ala Lys Trp Ser Gln Ala Ala Pro Met Ala
            20                  25                  30

Glu Gly Gly Gly Gln Asn His His Glu Val Val Lys Phe Met Asp
            35                  40                  45

Val Tyr Gln Arg Ser Tyr Cys His Pro Ile Glu Thr Leu Val Asp
            50                  55                  60

Ile Phe Gln Glu Tyr Pro Asp Glu Ile Glu Tyr Ile Phe Lys Pro
            65                  70                  75

Ser Cys Val Pro Leu Met Arg Cys Gly Gly Cys Cys Asn Asp Glu
            80                  85                  90

Gly Leu Glu Cys Val Pro Thr Glu Glu Ser Asn Ile Thr Met Gln
            95                 100                 105

Ile Met Arg Ile Lys Pro His Gln Gly Gln His Ile Gly Glu Met
           110                 115                 120

Ser Phe Leu Gln His Asn Lys Cys Glu Cys Arg Pro Lys Lys Asp
           125                 130                 135

Arg Ala Arg Gln Glu Asn Pro Cys Gly Pro Cys Ser Glu Arg Arg
           140                 145                 150

Lys His Leu Phe Val Gln Asp Pro Gln Thr Cys Lys Cys Ser Cys
           155                 160                 165

Lys Asn Thr Asp Ser Arg Cys Lys Ala Arg Gln Leu Glu Leu Asn
           170                 175                 180

Glu Arg Thr Cys Arg Cys Asp Lys Pro Arg Arg
           185                 190

<210> SEQ ID NO 3
<211> LENGTH: 6
<212> TYPE: DNA
<213> ORGANISM: Artificial sequence
<220> FEATURE:
<223> OTHER INFORMATION: sequence is synthesized
<220> FEATURE:
<221> NAME/KEY: CAAT_signal modified_base
<222> LOCATION: 2
<223> OTHER INFORMATION: n at position 2 may be A, G, C or T

<400> SEQUENCE: 3 cncaat                                                              6

<210> SEQ ID NO 4
<211> LENGTH: 6
<212> TYPE: DNA
```

<213> ORGANISM: Artificial sequence
<220> FEATURE:
<223> OTHER INFORMATION: sequence is synthesized
<220> FEATURE:
<221> NAME/KEY: polyA_signal
<222> LOCATION: full
<223> OTHER INFORMATION: polyadenylation signal

<400> SEQUENCE: 4 aataaa                                                                6

<210> SEQ ID NO 5
<211> LENGTH: 29
<212> TYPE: DNA
<213> ORGANISM: Artificial sequence
<220> FEATURE:
<223> OTHER INFORMATION: sequence is synthesized

<400> SEQUENCE: 5
agcgaagcta ctgccatccg attgagacc                                       29

<210> SEQ ID NO 6
<211> LENGTH: 38
<212> TYPE: DNA
<213> ORGANISM: Artificial sequence
<220> FEATURE:
<223> OTHER INFORMATION: sequence is synthesized

<400> SEQUENCE: 6
tgatgcgctg tggaggctgc tgtaacgatg aaggcctg                             38

<210> SEQ ID NO 7
<211> LENGTH: 49
<212> TYPE: DNA
<213> ORGANISM: Artificial sequence
<220> FEATURE:
<223> OTHER INFORMATION: sequence is synthesized

<400> SEQUENCE: 7
tgtaacgatg aaggcctgga gtgcgtgcgt gcccacggaa gagagcaac                 49

<210> SEQ ID NO 8
<211> LENGTH: 36
<212> TYPE: DNA
<213> ORGANISM: Artificial sequence
<220> FEATURE:
<223> OTHER INFORMATION: sequence is synthesized

<400> SEQUENCE: 8
atcaaacctc accaaggcca gcacatagga gagatg                               36

<210> SEQ ID NO 9
<211> LENGTH: 37
<212> TYPE: DNA
<213> ORGANISM: Artificial sequence
<220> FEATURE:
<223> OTHER INFORMATION: sequence is synthesized

<400> SEQUENCE: 9
tgagcttcct acagcacaac aaatgtgaat gcaggtg                              37

<210> SEQ ID NO 10
<211> LENGTH: 43
<212> TYPE: DNA
<213> ORGANISM: Artificial sequence
<220> FEATURE:
<223> OTHER INFORMATION: sequence is synthesized -continued

<400> SEQUENCE: 10
tgcagaccaa agaaagacag agcacggcaa gaaaagtaag tgg                    43

<210> SEQ ID NO 11
<211> LENGTH: 190
<212> TYPE: PRT
<213> ORGANISM: Artificial sequence
<220> FEATURE:
<223> OTHER INFORMATION: sequence is synthesized

<400> SEQUENCE: 11

Met Asn Phe Leu Leu Ser Trp Val His Trp Thr Leu Ala Leu Leu
 1               5                  10                  15

Leu Tyr Leu His His Ala Lys Trp Ser Gln Ala Ala Pro Thr Thr
                20                  25                  30

Glu Gly Glu Gln Lys Ser His Glu Val Ile Lys Phe Met Asp Val
                35                  40                  45

Tyr Gln Arg Ser Tyr Cys Arg Pro Ile Glu Thr Leu Val Asp Ile
                50                  55                  60

Phe Gln Glu Tyr Pro Asp Glu Ile Glu Tyr Ile Phe Lys Pro Ser
                65                  70                  75

Cys Val Pro Leu Met Arg Cys Ala Gly Cys Cys Asn Asp Glu Ala
                80                  85                  90

Leu Glu Cys Val Pro Thr Ser Glu Ser Asn Ile Thr Met Gln Ile
                95                 100                 105

Met Arg Ile Lys Pro His Gln Gly Gln His Ile Gly Glu Met Ser
               110                 115                 120

Phe Leu Gln His Ser Arg Cys Glu Cys Arg Pro Lys Lys Asp Arg
               125                 130                 135

Thr Lys Pro Glu Asn His Cys Glu Pro Cys Ser Glu Arg Arg Lys
               140                 145                 150

His Leu Phe Val Gln Asp Pro Gln Thr Cys Lys Cys Ser Cys Lys
               155                 160                 165

Asn Thr Asp Ser Arg Cys Lys Ala Arg Gln Leu Glu Leu Asn Glu
               170                 175                 180

Arg Thr Cys Arg Cys Asp Lys Pro Arg Arg
               185                 190

<210> SEQ ID NO 12
<211> LENGTH: 190
<212> TYPE: PRT
<213> ORGANISM: Artificial sequence
<220> FEATURE:
<223> OTHER INFORMATION: sequence is synthesized

<400> SEQUENCE: 12

Met Asn Phe Leu Leu Ser Trp Val His Trp Thr Leu Ala Leu Leu
 1               5                  10                  15

Leu Tyr Leu His His Ala Lys Trp Ser Gln Ala Ala Pro Thr Thr
                20                  25                  30

Glu Gly Glu Gln Lys Ser His Glu Val Ile Lys Phe Met Asp Val
                35                  40                  45

Tyr Gln Arg Ser Tyr Cys His Pro Ile Glu Thr Leu Val Asp Ile
                50                  55                  60

Phe Gln Glu Tyr Pro Asp Glu Ile Glu Tyr Ile Phe Lys Pro Ser
                65                  70                  75

Cys Val Pro Leu Met Arg Cys Gly Gly Cys Cys Asn Asp Glu Gly
                80                  85                  90

-continued

```
Leu Glu Cys Val Pro Thr Glu Glu Ser Asn Ile Thr Met Gln Ile
            95                  100                 105

Met Arg Ile Lys Pro His Gln Gly Gln His Ile Gly Glu Met Ser
            110                 115                 120

Phe Leu Gln His Asn Lys Cys Glu Cys Arg Pro Lys Lys Asp Arg
            125                 130                 135

Ala Arg Gln Glu Asn His Cys Glu Pro Cys Ser Glu Arg Arg Lys
            140                 145                 150

His Leu Phe Val Gln Asp Pro Gln Thr Cys Lys Cys Ser Cys Lys
            155                 160                 165

Asn Thr Asp Ser Arg Cys Lys Ala Arg Gln Leu Glu Leu Asn Glu
            170                 175                 180

Arg Thr Cys Arg Cys Asp Lys Pro Arg Arg
            185                 190
```

TRANSGENIC MICE EXPRESSING HUMANIZED VEGF

RELATED APPLICATIONS

This application is a National Stage of Application No. PCT/US2007/088537, filed 21-Dec.-2007, which claims priority under 35 USC 119(e) to provisional application No. 60/871,736, filed 22-Dec.-2006, the contents of which are incorporated herein by reference.

FIELD OF THE INVENTION

This present invention generally relates to transgenic animals also useful to study VEGF-related therapies. Specifically, the invention relates to humanized VEGF and non-human transgenic animals expressing it.

BACKGROUND OF THE INVENTION

Angiogenesis is an important cellular event in which vascular endothelial cells proliferate, prune and reorganize to form new vessels from the preexisting vascular network. There is compelling evidence that the development of a vascular supply is essential for normal and pathological proliferative processes (Folkman and Klagsbrun (1987) Science 235:442-447). Angiogenesis is also implicated in the pathogenesis of a variety of disorders, including but not limited to, tumors, proliferative retinopathies, age-related macular degeneration, rheumatoid arthritis (RA), and psoriasis. Angiogenesis is essential for the growth of most primary tumors and their subsequent metastasis.

In view of the remarkable physiological and pathological importance of angiogenesis, much work has been dedicated to the elucidation of the factors capable of regulating this process. It is suggested that the angiogenesis process is regulated by a balance between pro- and anti- angiogenic molecules, and is derailed in various diseases, especially cancer. Carmeliet and Jain (2000) Nature 407:249-257.

Vascular endothelial cell growth factor (VEGF), which is also termed VEGF-A or vascular permeability factor (VPF), has been reported as a pivotal regulator of both normal and abnormal angiogenesis. Ferrara and Davis-Smyth (1997) Endocrine Rev. 18:4-25; Ferrara (1999) J. Mol. Med. 77:527-543. Compared to other growth factors that contribute to the processes of vascular formation, VEGF is unique in its high specificity for endothelial cells within the vascular system. VEGF is essential for embryonic vasculogenesis and angiogenesis. Carmeliet et al. (1996) Nature 380:435-439; Ferrara et al. (1996) Nature 380:439-442. Furthermore, VEGF is required for the cyclical blood vessel proliferation in the female reproductive tract and for bone growth and cartilage formation. Ferrara et al. (1998) Nature Med. 4:336-340; Gerber et al. (1999) Nature Med. 5:623-628.

In addition to being an angiogenic factor in angiogenesis and vasculogenesis, VEGF, as a pleiotropic growth factor, exhibits multiple biological effects in other physiological processes, such as endothelial cell survival, vessel permeability and vasodilation, monocyte chemotaxis and calcium influx. Ferrara and Davis-Smyth (1997), supra. Moreover, recent studies have reported mitogenic effects of VEGF on a few non-endothelial cell types, such as retinal pigment epithelial cells, pancreatic duct cells and Schwann cells. Guerrin et al. (1995) J. Cell Physiol. 164:385-394; Oberg-Welsh et al. (1997) Mol. Cell. Endocrinol. 126:125-132; Sondell et al. (1999) J. Neurosci. 19:5731-5740.

Substantial evidence also implicates VEGF's critical role in the development of conditions or diseases that involve pathological angiogenesis. The VEGF mRNA is overexpressed by the majority of human tumors examined (Berkman et al. J Clin Invest 91:153-159 (1993); Brown et al. Human Pathol. 26:86-91 (1995); Brown et al. Cancer Res. 53:4727-4735 (1993); Mattern et al. Brit. J. Cancer. 73:931-934 (1996); and Dvorak et al. Am J. Pathol. 146:1029-1039 (1995)). Also, the concentration of VEGF in eye fluids is highly correlated to the presence of active proliferation of blood vessels in patients with diabetic and other ischemia-related retinopathies (Aiello et al. N. Engl. J. Med. 331:1480-1487 (1994)). Furthermore, studies have demonstrated the localization of VEGF in choroidal neovascular membranes in patients affected by AMD (Lopez et al. Invest. Ophtalmo. Vis. Sci. 37:855-868 (1996)).

Given its central role in promoting tumor growth, VEGF provides an attractive target for therapeutic intervention. Indeed, a variety of therapeutic strategies aimed at blocking VEGF or its receptor signaling system are currently being developed for the treatment of neoplastic diseases. Rosen (2000) Oncologist 5:20-27; Ellis et al. (2000) Oncologist 5:11-15; Kerbel (2001) J. Clin. Oncol. 19:45S-51S. The anti-VEGF antibody "bevacizumab", also known as "rhuMAb VEGF" or "AVASTIN®", is a recombinant humanized anti-VEGF monoclonal antibody generated according to Presta et al. (1997) Cancer Res. 57:4593-4599. Bevacizumab is approved for treatment of metastatic colorectal cancer and non-small cell lung cancer and is being investigated clinically for treating various other cancers.

In spite of the significant roles of VEGF in normal and pathological angiogenesis, animal models are lacking which can be used to study human VEGF. Thus, a need exists for relevant animal models for disease study and pharmaceutical drug development.

SUMMARY OF THE INVENTION

The present invention generally relates to non-naturally occurring non-human transgenic animals expressing human or humanized VEGF. In one aspect, the transgenic animals provide a system to identify and test novel therapeutic agents for VEGF associated diseases or conditions, such as cancer. In some embodiments, the transgenic animals are useful to test efficacy and safety of VEGF directed therapies.

In one aspect, the invention provides a non-human transgenic animal expressing humanized VEGF. In some embodiments, the humanized VEGF is human VEGF, hum-I VEGF, or hum-X VEGF. In some embodiments, the animal is a rodent, e.g. a mouse. In some embodiments the invention provides a cell or tissue derived from a non-human transgenic animal expressing humanized VEGF.

In another aspect, the invention provides a nucleic acid molecule comprising a nucleotide sequence encoding hum-I VEGF or hum-X VEGF as well as a polypeptide encoded by it. In some embodiments, the invention provides a vector comprising the nucleic acid molecule. In some embodiments, the invention provides a host cell comprising the nucleic acid molecule or a vector comprising it. In some embodiments, the invention provides a method of producing hum-I VEGF or hum-X VEGF comprising culturing the host cell.

In another aspect, the invention provides a method of identifying a compound as a possible agent for treating a VEGF-mediated disease said method comprising: a) measuring the level of VEGF in the non-human transgenic animal of any one of claims 1-5; b) administering said compound to the animal; and c) measuring the level of VEGF in the animal; wherein an alteration in the level of VEGF after administration with the agent identifies the compound as a possible agent for treating a VEGF-mediated disease.

In another aspect, the invention provides a method of identifying a VEGF antagonist as a possible agent for treating a human cancer said method comprising: a) administering said agent to the non-human transgenic animal of any one of claims 1-5, wherein said animal has a human cancer cell tumor xenograft; and b) monitoring growth of said xenograft; wherein a reduction in growth rate or size of said xenograft identifies the VEGF antagonist as a possible agent for treating a human cancer. In some embodiments, the VEGF antagonist is an antibody.

In another aspect, the invention provides a method of testing safety of a VEGF antagonist, said method comprising: a) administering said VEGF antagonist to the animal of claim 1 or 2; and b) monitoring the animal for short or long term adverse effects. In some embodiments, the VEGF antagonist is an antibody.

BRIEF DESCRIPTION OF THE FIGURES

FIG. 2A shows growth curves of Calu-6 tumors. The treatment started three days after implantation with either control, B20-4.1, G6-31, bevacizumab or Y0317 Mabs (5 mg/kg, IP, twice weekly).

FIG. 2F shows terminal tumor weights of Calu-6 tumor on day 63 of treatment with various anti-VEGF Mabs. Tumors treated with B20-4.1 and G6-31 displayed significantly reduced weight compared to bevacizumab treated tumors.

FIG. 2G shows tumor growth curves of human colorectal tumor (HM7) treated after tumor-volumes reached 500mm$^3$ (regression experiment) with either control, B20-4.1, G6-31, bevacizumab or Y0317 antibody (5 mg/kg, IP, twice weekly).

DETAILED DESCRIPTION

Figure 1A:
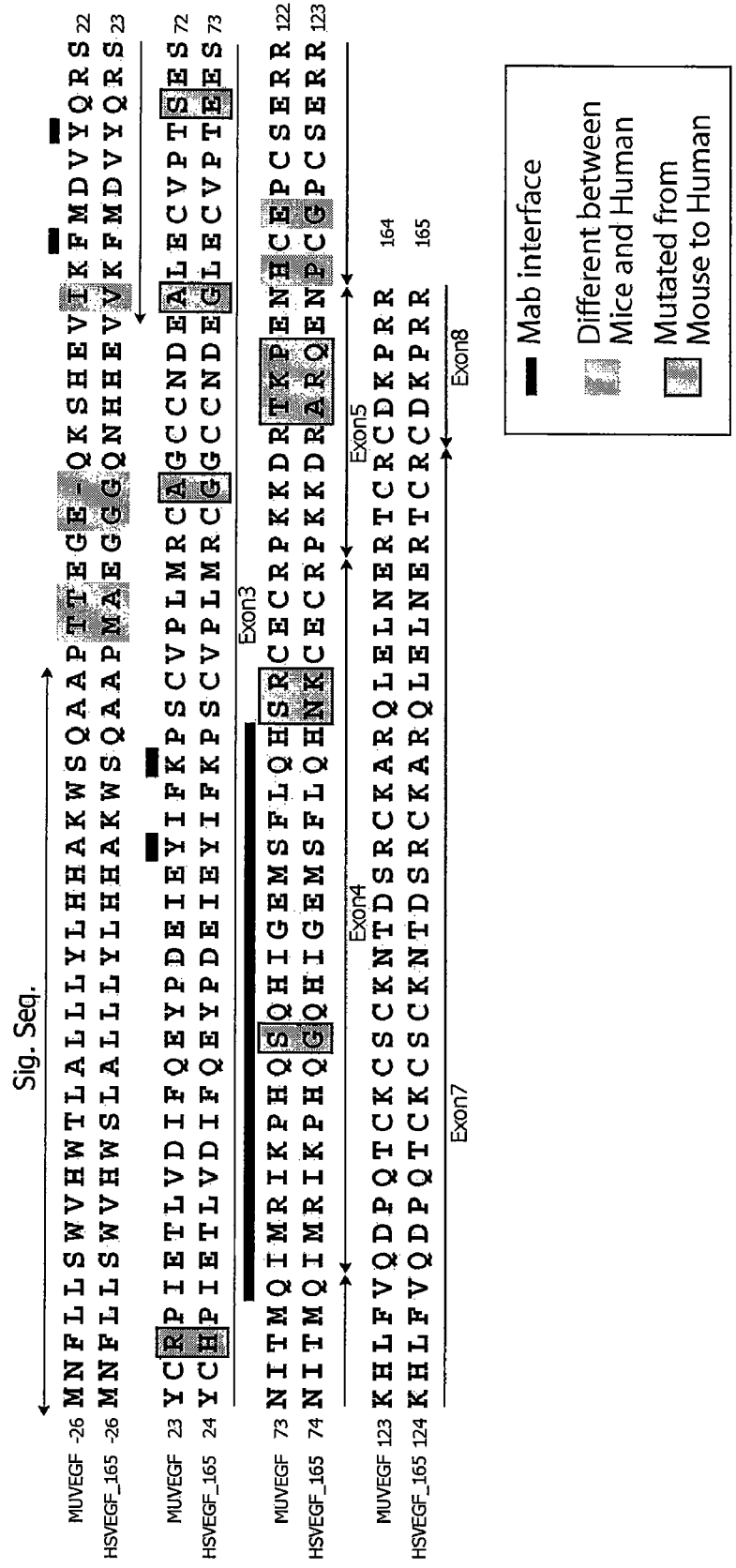
FIG. 1A shows a sequence comparison between mouse (SEQ ID NO: 1) and human VEGF-A (SEQ ID NO: 2). Amino acids that are different between murine VEGF164 and human VEGF165 are shaded grey. 10 amino acids (boxed and grey) of mouse VEGF were mutated to human residues by site-directed mutagenesis to generate the hum-X VEGF sequence.
Figure 1B:
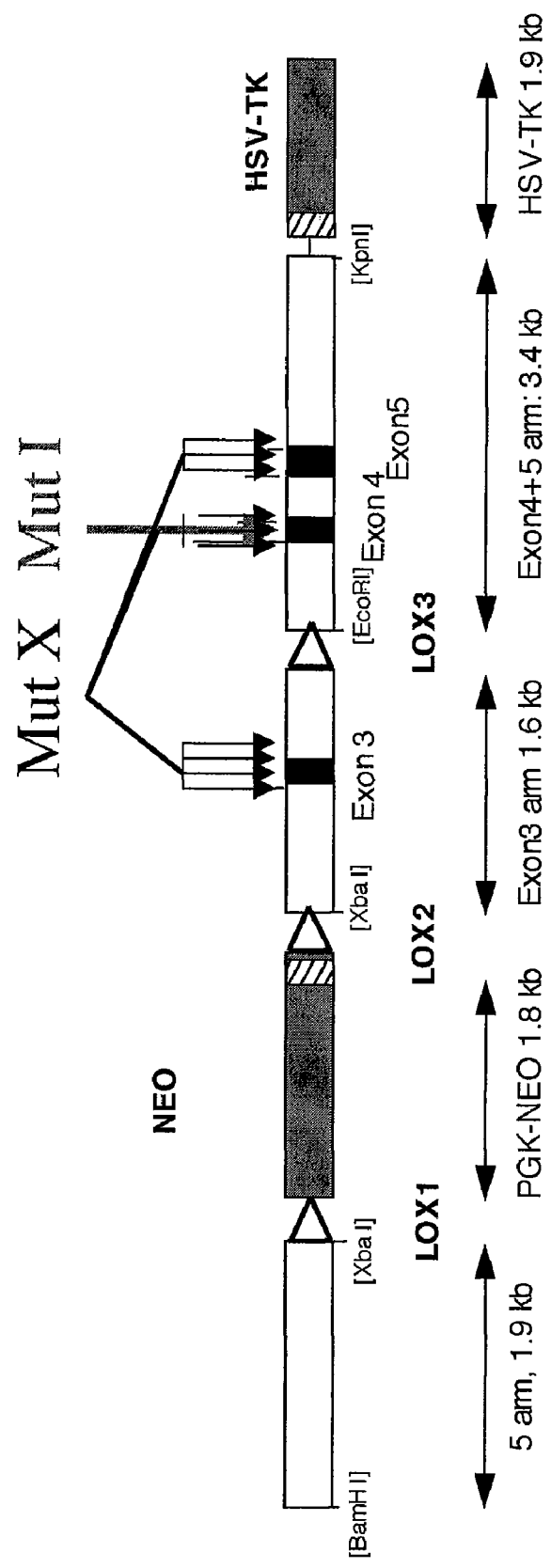
FIG. 1B shows a schematic representation of the targeting vectors to generate hum-I and hum-X knock-in (ki) mice. Mutations were introduced in exons 3 to 5 of the targeting vectors, resulting in mice expressing the hum-I or hum-X VEGF form. Hum-I VEGF protein consists of the mutation muVEGF-S87G. Hum-X VEGF protein consists of the following mutations: muVEGF-R26H, A57G, A64G, S71E, S87G, S99N, R100K, T110A, K111R, P112Q. This nomenclature starts from the mature sequence.

The following terms have the meanings ascribed to them below unless specified otherwise.

The terms "VEGF" and "VEGF-A" are used interchangeably to refer to the 165-amino acid vascular endothelial cell growth factor and related 121-, 189-, and 206-amino acid vascular endothelial cell growth factors, as described by Leung et al. Science, 246:1306 (1989), and Houck et al. Mol. Endocrin., 5:1806 (1991), together with the naturally occurring allelic and processed forms thereof. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF165." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

An "anti-VEGF antibody" is an antibody that binds to VEGF with sufficient affinity and specificity. An anti-VEGF antibody can be used as a therapeutic agent in targeting and interfering with diseases or conditions where VEGF activity is involved. An anti-VEGF antibody will usually not bind to other VEGF homologues such as VEGF-B or VEGF-C, nor other growth factors such as P1GF, PDGF or bFGF.

A "VEGF antagonist" refers to a molecule capable of neutralizing, blocking, inhibiting, abrogating, reducing or interfering with VEGF activities including its binding to one or more VEGF receptors. VEGF antagonists include certain anti-VEGF antibodies and antigen-binding fragments thereof, receptor molecules and derivatives which bind specifically to VEGF thereby sequestering its binding from one or more receptors, anti-VEGF receptor antibodies and VEGF receptor antagonists such as small molecule inhibitors of the VEGFR tyrosine kinases.

The term "construct" or "targeting construct" refers to a polynucleotide molecule that comprises a targeting region. A targeting region comprises a sequence that is substantially homologous to an endogenous sequence in a target tissue, cell or animal and that provides for integration of the targeting construct into the genome of the target tissue, cell or animal Typically, the targeting construct will also include a gene or a nucleic acid sequence of particular interest, a marker gene and appropriate control sequences.

"Disruption" of a gene occurs when a fragment of DNA locates and recombines with an endogenous homologous sequence. These sequence disruptions or modifications may include insertions, missense, frameshift, deletion, or substitutions, or replacements of DNA sequence, or any combination thereof. Insertions include the insertion of entire genes, which may be of animal, plant, fungal, insect, prokaryotic, or viral origin. Disruption, for example, can alter the normal gene product by inhibiting its production partially or completely or by enhancing the normal gene product's activity or by altering its sequence.

The term "endogenous loci" is meant to include the naturally occurring genetic loci found in the host animal that is to become transgenic.

The term "heterologous" when used in conjunction with polypeptide or gene refers to a polypeptide having an amino acid sequence or a DNA encoding the polypeptide that is not found in transgenic nonhuman host animal. Thus, a transgenic mouse having a humanized VEGF gene can be described as having a heterologous VEGF gene. The transgene can be detected using a variety of methods including PCR, Western blot, or Southern blot.

The term "non-human animals" is intended to include any vertebrate such as mammals, birds, reptiles, and amphibians. Suitable mammals include, e.g., rodents, non-human primates, sheep, dogs and cows. Suitable birds include, e.g., chickens, geese, and turkeys. Preferred non-human animals are selected from the rodent family including rat and mouse, most preferably mouse.

The term "naturally-occurring" or "naturally associated" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Transcriptional regulatory sequence" refers to polynucleotide sequences, such as initiation signals, enhancers, and promoters, which induce or control transcription of protein coding sequences with which they are operably linked In preferred embodiments, transcription of a recombinant transgene is under the control of a promoter sequence (or other transcriptional regulatory sequence), which controls the expression of the recombinant gene in a cell-type in which expression is intended. It will also be understood that the recombinant gene can be under the control of transcriptional regulatory sequences which are the same or which are different from those sequences, which control transcription of a naturally-occurring form of VEGF.

As used herein, the term "transgene" means a nucleic acid sequence (encoding, e.g., humanized VEGF) that has been introduced into a cell by way of human intervention such as by way of the described methods herein. A transgene could be partly or entirely heterologous, i.e., foreign, to the transgenic animal or cell into which it is introduced. A transgene can include one or more transcriptional regulatory sequences and any other nucleic acid, such as introns, that may be necessary for optimal expression of a selected nucleic acid.

"Transgenic animal" or "Tg+" are used interchangeably and are intended to include any non-naturally occurring non-human animal in which one or more of the cells of the animal contain heterologous nucleic acid encoding human or humanized VEGF, that has been introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, but rather is directed to the introduction of a recombinant DNA molecule. This molecule may be integrated within a chromosome, or it may be extrachromosomally replicating DNA. The term "Tg+" includes animals that are heterozygous and/or homozygous for human or humanized VEGF.

"VEGF associated disease" refers to diseases or disorders that have been associated with the expression of VEGF or can be treated with a VEGF antagonist. For example, a chimeric anti-VEGF antibody has been used to treat patients with certain cancers. An additional example is the use of anti-VEGF therapy to treat age-related macular degeneration.

A. Modes of the Invention

The present invention provides a transgenic animal expressing human or humanized VEGF. These animals may be used to study the efficacy, pharmacokinetic, pharmacodynamic, and safety properties of VEGF directed therapies. These animal models can be used for screening of agents including, e.g., VEGF antagonists, including but not limited to antibodies against VEGF.

B. DNA Constructs

The invention also provides isolated nucleic acid encoding a human or humanized VEGF as disclosed herein, vectors and host cells comprising the nucleic acid, and recombinant techniques for their production.

For recombinant protein production, the nucleic acid encoding it is isolated and inserted into a replicable vector for further cloning (amplification of the DNA) or for expression. DNA encoding the human or humanized VEGF is readily isolated and sequenced using conventional procedures (e.g., by using oligonucleotide probes that are capable of binding specifically to genes encoding the polypeptide variant). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

A polypeptide of this invention may be produced recombinantly not only directly, but also as a fusion polypeptide with a heterologous polypeptide, which may be preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native polypeptide variant signal sequence, the signal sequence is substituted by a prokaryotic signal sequence selected, for example, from the group of the alkaline phosphatase, penicillinase, 1pp, or heat-stable enterotoxin II leaders. For yeast secretion the native signal sequence may be substituted by, e.g., the yeast invertase leader, a factor leader (including Saccharomyces and Kluyveromyces α-factor leaders), or acid phosphatase leader, the C. albicans glucoamylase leader, or the signal described in WO 90/13646. In mammalian cell expression, mammalian signal sequences as well as viral secretory leaders, for example, the herpes simplex gD signal, are available. The DNA for such precursor region is ligated in reading frame to DNA encoding the polypeptide.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the polypeptide variant nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding polypeptide variant, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC® No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC® 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for K. lactis. Van den Berg, Bio/Technology, 8:135 (1990). Stable multi-copy expression vectors for secretion of mature recombinant human serum albumin by industrial strains of Kluyveromyces have also been disclosed. Fleer et al., Bio/Technology, 9:968-975 (1991).

(iv) Promoter Component

Expression and cloning vectors usually contain a promoter that is recognized by the host organism and is operably linked to the nucleic acid encoding a polypeptide of the invention. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the polypeptide variant.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide (SEQ ID NO: 3). At the 3' end of most eukaryotic genes is an AATAAA sequence (SEQ ID NO: 4) that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

The polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the rows sarcoma virus long terminal repeat can be used as the promoter.

(v) Enhancer Element Component

Transcription of a DNA encoding the polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the polypeptide-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide variant. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), Pseudomonas such as P. aeruginosa, and Streptomyces. One preferred *E. coli* cloning host is *E. coli* 294 (ATCC® 31,446), although other strains such as *E. coli* B, *E.* coli X1776 (ATCC® 31,537), and *E. coli* W3110 (ATCC® 27,325) are suitable. These examples are illustrative rather than limiting.

In addition to prokaryotes, eukaryotic microbes such as filamentous fungi or yeast are suitable cloning or expression hosts for polypeptide variant-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC® 12,424), *K. bulgaricus* (ATCC® 16,045), *K. wickeramii* (ATCC® 24,178), *K. waltii* (ATCC® 56,500), *K. drosophilarum* (ATCC® 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated polypeptide variant are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC® CRL 1651); human embryonic kidney line (293 or 293 cells subcloned for growth in suspension culture, Graham et al., J. Gen Virol. 36:59 (1977)); baby hamster kidney cells (BHK, ATCC® CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC® CCL 70); African green monkey kidney cells (VERO-76, ATCC® CRL-1587); human cervical carcinoma cells (HELA, ATCC® CCL 2); canine kidney cells (MDCK, ATCC® CCL 34); buffalo rat liver cells (BRL 3A, ATCC® CRL 1442); human lung cells (W138, ATCC® CCL 75); human liver cells (Hep G2, HB 8065); human mammary cells (HEK293), mouse mammary tumor (MMT 060562, ATCC® CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

(viii) Culturing the Host Cells

The host cells used to produce a polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem.102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

C. Production of Transgenic Animals

Methods for generating transgenic animals of the present invention are well known in the art (see, generally, Gene Targeting: A Practical Approach, Joyner, ed., Oxford University Press, Inc. (2000)). In one embodiment, generation of the transgenic mice may optionally involve disruption of murine VEGF and introduction of the gene encoding human or humanized VEGF into the murine genome, preferably at the same location as endogenous VEGF. According to some embodiments of the invention, a transgenic mouse model is generated where specific amino acids of human VEGF have been introduced into murine VEGF (e.g. human VEGF, hum-I VEGF, hum-X VEGF, etc.).

The transgenic non-human animals of the invention are preferably produced by introducing transgenes into the germline of the animal. Embryonic target cells at various developmental stages can be used to introduce transgenes. Different methods are used depending on the stage of development of the embryonic target cell. The specific line(s) of any animal used to practice this invention are selected for general good health, good embryo yields, good pronuclear visibility in the embryo, and good reproductive fitness. When transgenic mice are to be produced, strains such as C57BL/6 or C57BL/6×DBA/2 $F_1$, or FVB lines are often used (obtained commercially from Charles River Labs, Boston, Mass., The Jackson Laboratory, Bar Harbor, Me., or Taconic Labs.). In addition, nude mice may be employed to provide for introduction of human tumor cells into the transgenic mice. Breeding and maintenance of transgenic nude mice are more difficult because the mice are more susceptible to infection and disease.

Introduction of the transgene into the embryo can be accomplished by any means known in the art such as, for example, microinjection, electroporation, or lipofection. For example, the transgene can be introduced into a mammal by microinjection of the construct into the pronuclei of the fertilized mammalian egg(s) to cause one or more copies of the construct to be retained in the cells of the developing mammal(s), Following introduction of the transgene construct into the fertilized egg, the egg may be incubated in vitro for varying amounts of time, or reimplanted into the surrogate host, or both. In vitro incubation to maturity is within the scope of this invention. One common method is to incubate the embryos in vitro for about 1-7 days, depending on the species, and then reimplant them into the surrogate host.

Reimplantation is accomplished using standard methods. Usually, the surrogate host is anesthetized, and the embryos are inserted into the oviduct. The number of embryos implanted into a particular host will vary by species, but will usually be comparable to the number of offspring the species naturally produces.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260-1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927-6931; Van der Putten et al. (1985) PNAS 82:6148-6152). Transfection is easily and efficiently obtained by culturing the blastomeres on a monolayer of virus-producing cells (Van. der Putten, supra; Stewart et al. (1987) EMBO J. 6:383-388). Alternatively, infection can be performed at a later stage. Virus or virus-producing cells can be injected into the blastocoele (Jahner et al. (1982) Nature 298:623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonic stem cell. Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal In one embodiment of the invention, an endogenous VEGF gene in a nonhuman host is functionally disrupted by homologous integration of a heterologous humanized VEGF (including fully human VEGF), such that the heterologous VEGF gene substantially replaces the endogenous VEGF gene, and preferably completely replaces the coding sequences of the endogenous VEGF gene. Preferably, the heterologous humanized VEGF gene is linked, as a consequence of homologous integration, to regulatory sequences (e.g., an enhancer/promoter) of the endogenous VEGF gene, respectively, so that the heterologous gene is expressed under the transcriptional control of regulatory elements from the endogenous VEGF gene locus. Nonhuman hosts which are homozygous for such replacement alleles may be produced according to methods described herein. Such homozygous nonhuman hosts generally will express a heterologous humanized VEGF but do not express the endogenous VEGF protein. Usually, the expression pattern of the heterologous humanized VEGF gene will substantially mimic the expression pattern of the endogenous VEGF gene, in the naturally-occurring (non-transgenic) nonhuman host.

For example, a transgenic mouse can be generated that has human VEGF gene sequences in place of endogenous murine VEGF gene sequences and which are transcriptionally controlled by endogenous murine regulatory sequences. The humanized VEGF generally will be expressed similarly to the murine VEGF in naturally occurring non-transgenic mice.

Generally, a replacement-type targeting construct is employed for homologous gene replacement. Double-crossover homologous recombination between endogenous VEGF gene sequences of the targeting construct result in targeted integration of the heterologous VEGF gene segments. Usually, the homology targeting regions of the transgene comprise sequences which flank the endogenous VEGF gene segments, so that homologous recombination results in concomitant deletion of the endogenous VEGF, and homologous integration of the heterologous gene segments. Substantially an entire endogenous VEGF gene may be replaced with a heterologous VEGF by a single targeting event or by multiple targeting events (e.g., sequential replacement of individual exons). One or more selectable markers, usually in the form of positive or negative selection expression cassettes, may be positioned in the targeting construct. It is usually preferred that selectable markers are located intron regions of the heterologous replacement region.

Transgenic animals comprising transgene humanized VEGF can be crossed with other animals. In one embodiment, a transgenic mouse comprises the human VEGF and lacks the murine RAG2. A manner of preparation is to generate a series of mammals, each containing one of the desired knockout constructs or transgenes. Such mammals are bred together through a series of crosses, backcrosses and selections, to ultimately generate a single mammal containing all desired knockout constructs and/or transgenes, where the mammal is otherwise congenic (genetically identical) to the wild type except for the presence of the knockout(s) constructs and/or transgene(s).

Typically, crossing and backcrossing is accomplished by mating siblings or a parental strain with an offspring, depending on the goal of each particular step in the breeding process. In certain cases, it may be necessary to generate a large number of offspring in order to generate a single offspring that contains each of the knockout constructs and/or transgenes in the proper chromosomal location. In addition, it may be necessary to cross or backcross over several generations to ultimately obtain the desired genotype.

D. Verification of the Presence of Transgenes

Transgenic offspring of the surrogate host may be screened for the presence and/or expression of the transgene in the desired tissue, cell or animal by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as immunological assays, flow cytometric analysis, and the like.

E. Uses of Transgenic Animals

Transgenic animals of the present invention represent models of VEGF expression and function in humans. Accordingly, these animals are useful in studying the mechanisms behind VEGF function and related events, and to generate and test products (e.g., antibodies, bispecifics, multispecifics, etc.) useful in treating and diagnosing VEGF associated human diseases, including cancer and other angiogenesis related conditions.

In some embodiments, transgenically expressed humanized VEGF retains similar functional properties as are exhibited in humans. For example, heterologous humanized VEGF functionally replaces the animal's homologous VEGF and in addition is recognized by anti-human VEGF antibodies. Accordingly, in one embodiment the transgenic animals of the invention are used to test agents such as antibodies, multi- or bispecific molecules, immunoadhesins (e.g., for human safety and efficacy) for binding to target epitopes, such as a region of a human VEGF. Other agents can include antigen binding fragments of antibodies with or without Fc regions, single chain antibodies, minibodies (heavy chain only antibodies), heteromultimeric immunoadhesins with one of the multimers anti-human VEGF antigen binding region. Other agents may include small molecule VEGF antagonists. Accordingly, the present invention provides methods of identifying agents capable of treating a VEGF related disease.

A non-human transgenic animal of the present invention can further provide an indication of the safety of a particular agent for administration to a human. For example, a humanized antibody or other agent can be administered to the transgenic animal and any toxic or adverse effects as a result of the administration of the agent to the animal can be monitored or identified as an indication of the safety and tolerability of the humanized antibody or agent for in vivo human use. Adverse events that may occur on a short term basis include headache, infection, fever, chills, pain, nausea, asthenia, pharyngitis, diarrhea, rhinitis, infusion reactions, and myalgia. Short term adverse events are measured in days post treatment. Long term adverse effects include cytoxicity of certain cell types, bleeding events, release of mediators due to inflammatory and/or allergic reactions, inhibition of the immune system and/or development of an anti-therapeutic agent antibody, end organ toxicity, and increased incidence of infection or malignancy. Long term adverse events are measured in weeks or months post treatment.

Another aspect of the invention involves a method for determining efficacy of an anti-VEGF agent. Efficacy can be determined by administering a range of doses of the agent to set of transgenic animals having humanized VEGF, determining at least one dose that exhibits the desired effect.

The transgenic animals of the present invention, including cells, tissues, or other materials derived therefrom, can be utilized as models for diseases, especially diseases associated or mediated by VEGF. Animals of any species, including, but not limited to, mice, rats, rabbits, guinea pigs, pigs, micropigs, goats, and non-human primates, e.g., baboons, monkeys, and chimpanzees may be used to generate disease animal models. These systems may be used in a variety of applications. Such assays may be utilized as part of screening strategies designed to identify agents, such as compounds that are capable of ameliorating disease symptoms. Thus, the animal- and cell-based models may be used to identify drugs, pharmaceuticals, therapies and interventions that may be effective in treating disease.

Cell-based systems may be used to identify compounds that may act to ameliorate disease symptoms. For example, such cell systems may be exposed to a compound suspected of exhibiting an ability to ameliorate disease symptoms, at a sufficient concentration and for a time sufficient to elicit such an amelioration of disease symptoms in the exposed cells. After exposure, the cells are examined to determine whether one or more of the disease cellular phenotypes has been altered to resemble a more normal or more wild-type, non-disease phenotype.

Other uses will be readily apparent to one of skill in the art.

The following non-limiting examples are illustrative of the present invention.

EXAMPLES

Example 1

This example describes generation of humanized VEGF and transgenic (Tg+) mice expressing it.

Bevacizumab binds human VEGF, but not mouse VEGF. X-ray structure data, combined with site-directed mutagenesis, identified 3 different regions located within exons 3 and 4 of VEGF-A that are in direct contact with bevacizumab. The majority of these contacts are formed by residues of the β5-β6 loop (around residue 80), with 2 additional residues from the N-terminal helix and 2 residues from the α1-β2 loop (around residue 40) interacting at the margin of the interface (Muller et al. PNAS 94:7292-97 (1997), Muller et al. Structure 6:1153-67 (1998)) (FIG. 1A). With the exception of one residue, all the amino acids of human VEGF that are in contact with bevacizumab are conserved in mouse VEGF. The non-conserved residue, human Gly88, corresponds to Ser87 in the mouse VEGF sequence and is located in the core of the protein:antibody interface. The crystal structure of human VEGF-A in complex with the bevacizumab-Fab revealed that the interface between both molecules is tightly packed. Modeling of the serine side chain present in mouse VEGF, reveals that there is not enough room to accommodate the 2 additional non-hydrogen atoms that are introduced by the Gly88->Ser exchange. Previous studies demonstrated that mutation of glycine 88 to alanine (Gly88A1a) in human VEGF-A substantially reduced the binding of Mab A4.6.1, the murine precursor of bevacizumab (Muller et al. Structure 6:1153-67 (1998)). These observations suggested that introducing a single mutation Ser87Gly in mouse VEGF might be sufficient to restore binding to and neutralization by A4.6.1. However, the crystal structure of the complex and the mutagenesis analysis were performed using a truncated VEGF-A variant (8-109) (Muller et al. Structure 6:1153-67 (1998)). Therefore, the contribution of other residues, not present in VEGF8-109, to the binding of native VEGF-A by bevacizumab was unknown. Furthermore, phage derived antibodies such as G6 (G6-31) or B20-4 were known to contact additional non-conserved residues (Fuh et al. J. Biol. Chem. 281:6625-31 (2006)). These observations prompted us to also design a more extensively humanized murine VEGF-A that could be recognized by additional antibodies, and thus would allow us to test a broader variety of therapeutic compounds targeting VEGF signaling. We therefore generated two versions of "humanized" VEGF-A proteins. One mutant containing the single ser87gly mutation important for the binding of bevacizumab (hum-I VEGF), and a second form, hum-X VEGF, in which the 10 residues that are different in the receptor binding domain between murine and human VEGF-A are replaced by the respective amino acids in the human sequence (FIG. 1A). Thus, the sequences of hum-I VEGF and hum-X VEGF, including the signal sequence, are as follows:

```
hum-I VEGF (SEQ ID NO: 11):
MNFLLSWVHWTLALLLYLHHAKWSQAAPTTEGEQKSHEVIKFMDVYQRS        22

YCRPIETLVDIFQEYPDEIEYIFKPSCVPLMRCAGCCNDEALECVPTSES       72

NITMQIMRIKPHQGQHIGEMSFLQHSRCECRPKKDRTKPENHCEPCSERR       122

KHLFVQDPQTCKCSCKNTDSRCKARQLELNERTCRCDKPRR                164 hum-X VEGF (SEQ ID NO: 12):
MNFLLSWVHWTLALLLYLHHAKWSQAAPTTEGEQKSHEVIKFMDVYQRS        22

YCHPIETLVDIFQEYPDEIEYIFKPSCVPLMRCGGCCNDEGLECVPTEES       72

NITMQIMRIKPHQGQHIGEMSFLQHNKCECRPKKDRARQENHCEPCSERR       122

KHLFVQDPQTCKCSCKNTDSRCKARQLELNERTCRCDKPRR                164
```

We first tested whether hum-X VEGF retained the normal functions of VEGF. Recombinant hum-X VEGF, wild-type human and murine VEGF-A proteins were expressed in *E. coli* and purified. Pellets from bacterial cells expressing hum-X VEGF were resuspended in 10 volumes of 25 mM Tris, 5 mM EDTA, pH 7.5, with a Polytron® homogenizer. Cells were lysed by passing the cell suspension through a Microfluidizer® (Microfluidics International) and the solution was clarified by centrifugation. The pellet was resuspended in extraction buffer containing 7 M urea, 50 mM Hepes, 10 mM DTT, pH 8, and the solution was stirred at room temperature for 1 hr. The solution was centrifuged at 33,000×g for 30 minutes to remove insoluble cell debris and the supernatant containing denatured and reduced hum-X VEGF was diluted tenfold into refolding buffer (1 M urea, 50 mM Hepes, 15 mg/L dextran sulfate 8000, 0.05% Triton® X-100, pH 8.2). The refolding mixture was stirred overnight at room temperature and then centrifuged to remove precipitated protein Ammonium sulfate was added to 1 M concentration before loading the mixture onto a Phenyl TSK column equilibrated in 1 M ammonium sulfate, 25 mM Tris, pH 7.5; the hum-X VEGF was eluted with a decreasing ammonium sulfate gradient in this buffer to 0 M. hum-X VEGF containing fractions were pooled and further purified on a preparative C4 reversed phase column (Vydac). Fractions containing the dimeric hum-X VEGF were pooled and lyophilized.

We determined the relative affinities of bevacizumab and three 2nd-generation anti-human VEGF antibodies for native human VEGF-A, mouse VEGF-A, and the hum X VEGF protein. Antibody binding affinity was tested by surface plasmon resonance (SRP) measurement with a BIAcore™-3000 (BIAcore, Inc., Piscataway, N.J.). Carboxymethylated dextran biosensor chips (CM5, BIAcore Inc.) were activated with N-ethyl-N'-(3-dimethylaminopropyl)-carbodiimide hydrochloride (EDC) and N-hydroxysuccinimide (NHS) according to the supplier's instructions. Human VEGF-A, murine VEGF-A and hum-X VEGF was immobilized to achieve approximately 60 response units (RU). Two-fold serial dilutions of IgG (0.78-500 nM) were injected in PBS with 0.05% Tween® 20 (PBST) at 37° C. at a flow rate of 25 µl/min. Association rates ($k_{on}$) and dissociation rates ($k_{off}$) were calculated using one-to-one Langmuir binding model (BIAcore Evaluation Software version 3.2) by simultaneously fitting the association and dissociation sensorgram. The equilibrium dissociation constant (Kd) was derived as the ratio $k_{off}/k_{on}$.

As we hypothesized, the substitution of 10 human amino acids into the murine VEGF-A results in a protein that is recognized by all anti-human VEGF-A Mabs tested, with little change in affinity relative to wild-type human VEGF-A (Table 1; each measurement represents an average of three independent assay that vary <20%).

TABLE 1

Binding of antibodies to murine, human and humanized VEGF

|  | bevacizumab | Y0317 | B20-4.1 | G6-31 |
| --- | --- | --- | --- | --- |
| huVEGF$_{165}$ | 4.3 | 0.01 | 1.7 | 0.3 |
| Hum-X VEGF | 3.2 | 0.02 | 2.3 | 0.2 |
| muVEGF$_{164}$ | NB | 479 | 1.1 | 0.4 |

Next, we assessed the potencies of each VEGF-A variant to stimulate proliferation of primary endothelial cells in culture. Bovine retinal microvascular endothelial cells were seeded at a density of 500 cells per well in 96-well plates in growth medium (Low glucose DMEM supplemented with 10% calf serum, 2 mM glutamine, and antibiotics). After 6-7 days, cell growth was assayed with the use of Alamar B1ueTM (BioSource). Fluorescence was monitored at 530 nm excitation wavelength and 590 nm emission wavelength.

HuVEGF-A, muVEGF-A and hum-X VEGF stimulated bovine capillary endothelial cell proliferation at half maximal concentrations of 1.5, 0.6 and 0.9 ng/ml, respectively. Similar results were obtained with HUVEC cells. These findings indicated that the hum-X VEGF variant has potency comparable to that of wild-type human and murine VEGF-A proteins in stimulating EC proliferation in vitro.

Finally, we compared the potencies of the various anti-VEGF-A antibodies to interfere with endothelial cell proliferation induced by the various recombinant VEGF-A proteins. For inhibition assay, antibodies were added to the previous experiment at indicated concentrations before addition of VEGF and after 0.5-1 hr, hVEGF-A, mVEGF-A or MutX were added to a final concentration of 6 ng/mL IC$_{50}$ values were calculated using KaleidaGraph®. As expected, bevacizumab and Y0317 failed to block murine VEGF-A, while the IC$_{50}$ values of the remaining ligand/antibody pairs correlated well with antibody affinities (Table 2; data shown are means from triplicate experiments which varied by less than 20%).

TABLE 2

Inhibition of VEGF-stimulated bovine retinal capillary endothelial cell proliferation by bevacizumab, Y0317, B20-4.1 or G6-31 Mabs

|  | bevacizumab IC$_{50}$, (ng/mL) | Y0317 IC$_{50}$, (ng/mL) | B20-4.1 IC$_{50}$, (ng/mL) | G6-31 IC$_{50}$, (ng/mL) |
| --- | --- | --- | --- | --- |
| huVEGF165 | 32 | 0.75 | 52 | 4.9 |
| Hum-X VEGF | 55 | 2.7 | 76 | 6.1 |
| muVEGF164 | NA | NA | 500 | 3.8 |

These data confirmed that the hum-X, wild-type human and wild-type mouse VEGF-A proteins have comparable biological and biochemical properties, and that the ability of antibodies to interfere with the hum-X variant relative to wild-type human VEGF-A correlates with their respective affinities for the wild-type human protein.

Example 2

This example describes generation of transgenic (Tg+) mice expressing hum-X VEGF.

Having established the near equivalency of hum-X VEGF and wild-type murine VEGF-A in vitro, we proceeded to generate gene-targeting vectors to introduce 1 or 10 human amino acids into the mouse germline (FIG. 1F; hum-I VEGF and hum-X VEGF, respectively). 10 amino acids within the genomic targeting vector for VEGF-A consisting of exon 3, 4 and 5 of mouse VEGF-A (Gerber et al. Development 126: 1149-59 (1999)) were mutated from mouse to human sequences. For site directed mutagenesis of the residues located within exons 3, 4 and 5, the following oligonucleotides were used:

```
For exon 3:
Exon3-R/H:
                                   (SEQ ID NO: 5)
AGCGAAGCTACTGCCATCCGATTGAGACC, Exon3-A/G, A/G:
                                   (SEQ ID NO: 6)
TGATGCGCTGTGGAGGCTGCTGTAACGATGAAGGCCTG, Exon3-A/G, S/E:
                                   (SEQ ID NO: 7)
TGTAACGATGAAGGCCTGGAGTGCGTGCGTGCCCACGGA

AGAGAGCAAC.

For exon 4:
Exon4-S/G:
                                   (SEQ ID NO: 8)
ATCAAACCTCACCAAGGCCAGCACATAGGAGAGATG, Exon4-S/N, R/K:
                                   (SEQ ID NO: 9)
TGAGCTTCCTACAGCACAACAAATGTGAATGCAGGTG, Exon5-T/A, K/R, P/Q:
                                   (SEQ ID NO: 10)
TGCAGACCAAAGAAAGACAGAGCACGGCAAGAAA AGTAAGTGG.
```

The corresponding amino acids are: muVEGF-R26H, A57G, A64G, S71E, S87G, S99N, R100K, T110A, K111R, P112Q. Correct recombination events in ES cell were identified by PCR analysis and confirmed by Southern blot as described previously. Briefly, in correctly targeted ES cells, the neomycin resistance marker flanked by Lox-P sites was deleted by transient expression of Cre recombinase. Correct genomic recombination products were identified by genomic PCR and confirmed by Southern Blotting of the 3' and 5' flanking regions. ELISA experiments confirmed binding of A4.6.1 to hum-X VEGF protein present in conditioned media of targeted ES cells. In addition, the genomic DNA isolated from selected ES cell clones was digested with EcoRI and analyzed by Southern blotting as described previously (Gerber et al. (1999) supra) and by genomic sequencing to test for correct recombination events. One derivative of three different parental ES cell clones containing the floxed VEGF allele was used to generate chimeric mice by microinjection into the blastocoele cavity of 3.5-day C57BL/6N blastocysts (Hogan et al. Manipulating the Mouse Embryo: A Laboratory Manual, Cold Spring Harbor Press (1994)) Chimeric males were mated with C57BL/6N females and agouti offspring were screened for germline transmission by PCR analysis for VEGF alleles containing the loxP-1 and loxP-3 sites as described previously. Correct recombination events in embryonic stem cells (ES) were verified by Southern blotting experiments, genomic PCR, genomic sequencing and by determination of VEGF-A expression in targeted ES cells by ELISA.

Genotype frequency analysis of >500 knock-in (ki) mice revealed the expected Mendelian ratios of homozygous single mutant or 10-amino acid mutant (hum-X VEGF) mice, and no change in viability and survival of adult mice during a one year observation period was found. Based on the normal development and viability of both strains, we decided to conduct all further experiments in the more extensively humanized hum-X VEGF ki mice.

Example 3

This example demonstrates the use of transgenic hum-X VEGF mice for pharmacokinetic and therapeutic evaluation.

Recombinant murine VEGF-A and murine and human VEGFR1 and VEGFR2 proteins were purchased from R&D systems. Recombinant human VEGF-A (165-amino acid isoforms) was purified from E. coli at Genentech. 125-I-VEGF-A was purchased from Amersham.

Y0317, G6-31 and B20-4.1 Mabs were derived from human(ized) Fab phage libraries as described (Liang et al. J. Biol. Chem. 281:951-61 (2006)). Full-length human antibodies (hY0317, etc.) were generated by grafting the VH and VL variable domains from these Fabs onto the constant domains of human IgG1(kappa). For long-term administration in immunocompetent mice or for control experiments, full-length reverse-chimeric murine antibodies were generated by grafting the VH and VL variable domains onto the constant domains of murine IgG2a (kappa).

VEGF-A coat format to determine free anti-VEGF-A antibodies. MaxiSorpTM 96-well ELISA plates (Nunc, Roskilde, Denmark) were coated overnight with 0.5 µg/ml VEGF-A$_{165}$ in 50 mM sodium carbonate pH 9.6 at 100 µl/well. Plates were washed with PBS containing 0.05% polysorbate 20 and blocked with 150 µl/well of 0.5% bovine serum albumin, 10 ppm Proclin® 300 (Hyclone, Logan, UT) in PBS at room temperature for 1 hour. Two-fold serial dilutions of standards (0.0625-8 ng/ml of anti-VEGF mouse IgG2a, anti-VEGF human IgG1, or trap-human IgG1) in 0.05% BSA, 0.2% bovine μ-globulins (Sigma, St. Louis, Mo.), 0.25% CHAPS, 5 mM EDTA, 0.35M NaCl, 0.05% polysorbate 20 in PBS, pH 7.4 (samples buffer) and samples (minimum 1:20 dilution) were added to the plates at 100 μl/well. Plates were incubated at room temperature for 2 hours and washed. Bound mouse IgG2a antibodies and human IgG1 anti-VEGF-A antibodies were detected by adding 100 μl/well of anti-mouse IgG2a-HRP (Pharmingen, San Diego, Calif.) and anti-human FcHRP (Jackson ImmunoResearch, West Grove, Pa.), respectively. After a one hour incubation, plates were washed and the substrate 3,3',5,5'-tetramethyl benzidine (Kirkegaard and Perry Laboratories, Md.) was added (100 μl per well). The reaction was stopped by adding 1M $H_3PO_4$ (100 μl/well). The absorbance was read at 450 nm using a SpectraMax® 250 microplate reader (Molecular Devices Corp., Calif.). The titration curves were fit using a four-parameter regression curve-fitting program (KaleidaGraph®, Synergy software, Reading, Pa.). Data points within the range of the standard curve were used for calculating the anti-VEGF-A antibody concentrations in samples.

We compared the clearance of bevacizumab, Y0317, and hG6-31 after a single intravenous administration in homozygous hum-X VEGF ki mice and wild-type (hum-X VEGF wild-type) control littermates. The systemic clearance of bevacizumab in hum-X VEGF ki mice was about 3-fold faster than was observed in hum-X VEGF wild-type control littermates. In addition, clearance of both higher affinity Mabs (Y0317, G6-31) was about 3-fold increased relative to bevacizumab in hum-X VEGF ki mice. However, the clearance of G6-31 was similar between wild-type and hum-X VEGF ki mice, consistent with it being cross-reactive for both species. In contrast to the affinity-correlated clearance rates observed after a single antibody dose, bi-weekly administration of antibody for 2 to 10 weeks was associated with comparable levels of circulating antibodies in serum, but we found no correlation between antibody epitope or affinity. We hypothesize that the discrepancy in the antibody serum levels between single and multiple dose experiments may be due to the rapid binding of higher affinity Mabs to cell surface or extracellular matrix (ECM) bound VEGF-A, acting as a sink, and that such mechanism is saturable upon repeat dosing.

Figure 2B:
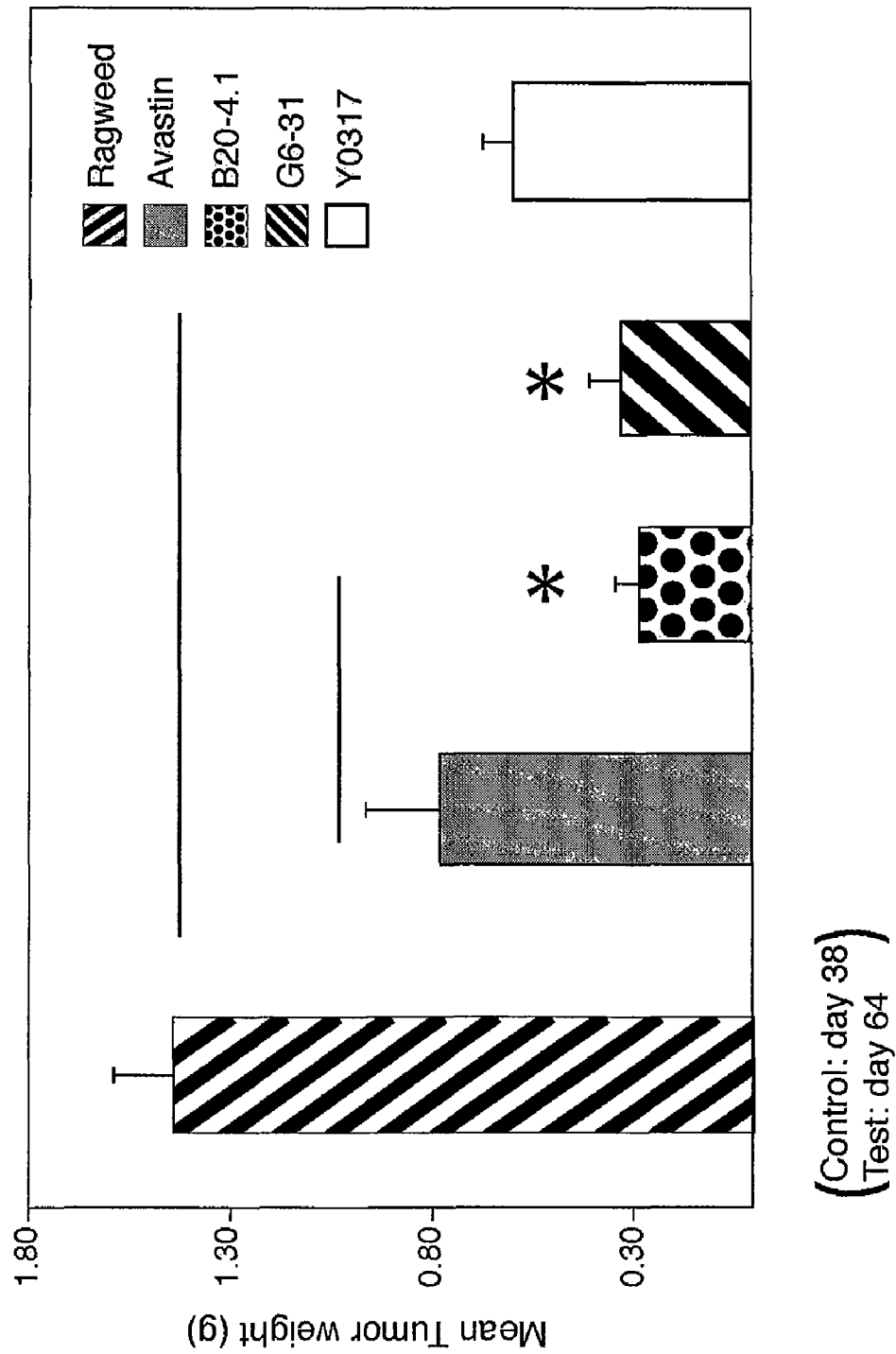
FIG. 2B shows terminal tumor weights of Calu-6 tumors on day 64 of treatment as described in FIG. 2A. B20-4.1 and G6-31 treated tumors were significantly smaller than bevacizumab treated tumors.
Figure 2C:
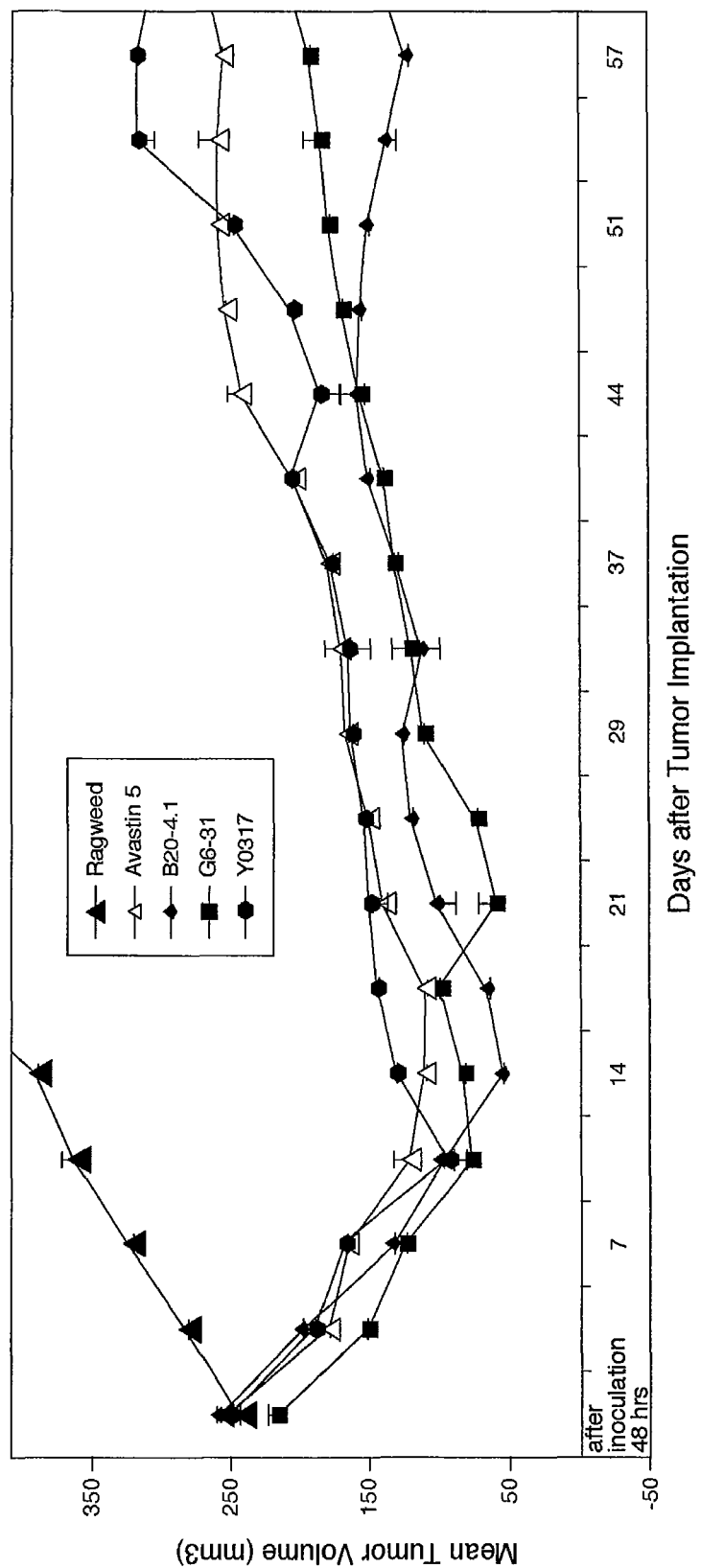
FIG. 2C shows growth curves of human colorectal carcinoma cells (HT29) treated on day 3 post implantation with either control, B20-4.1, G6-31, bevacizumab or Y0317 (5mg/kg, twice weekly, IP). Tumors treated with B20-4.1 and G6-31 were significantly smaller relative to bevacizumab-treated tumors at certain time-points during treatment.
Figure 2D:
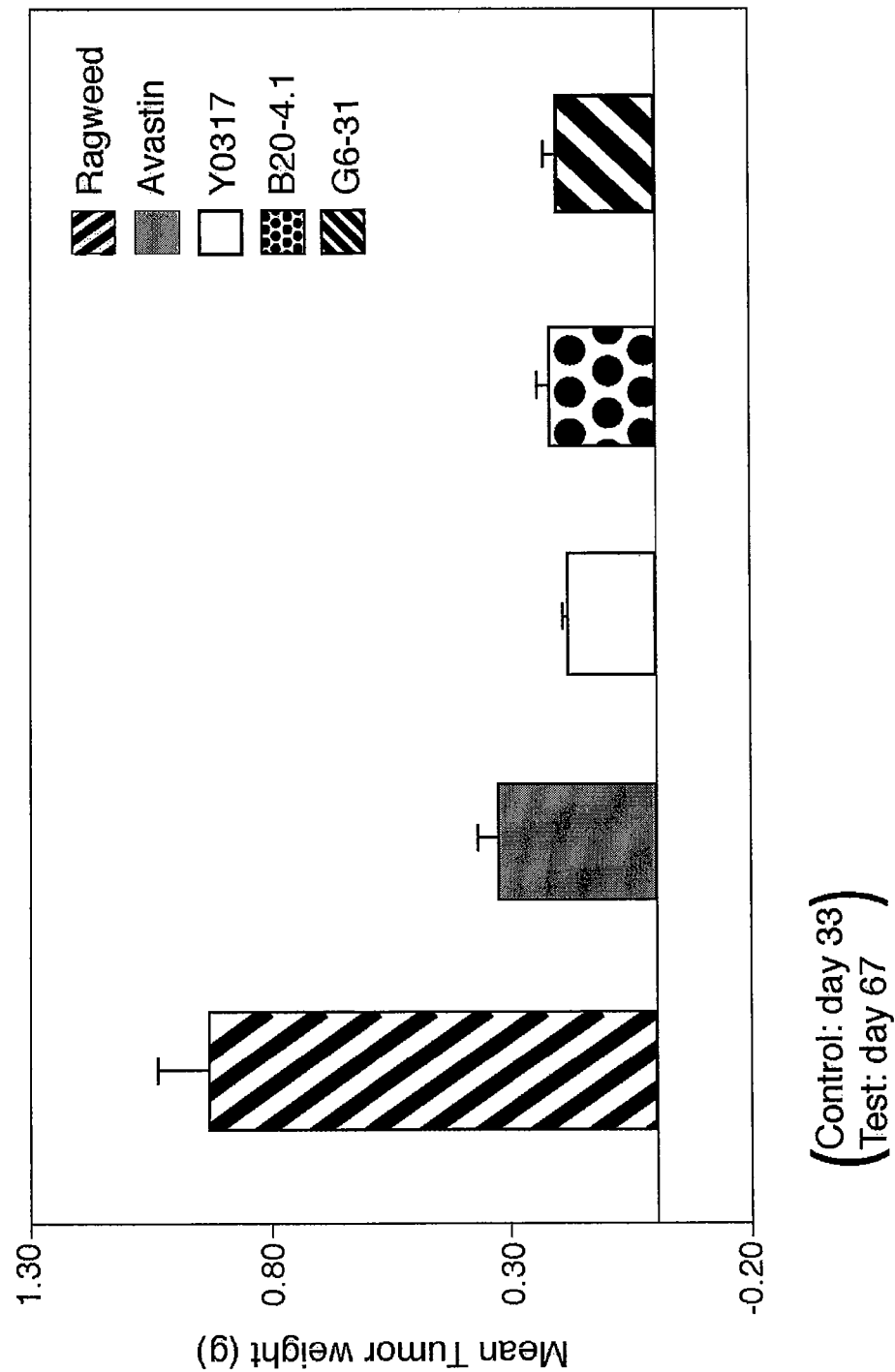
FIG. 2D shows terminal tumor weights of HT29 tumors on day 67 of treatment as described in FIG. 2C.
Figure 2E:
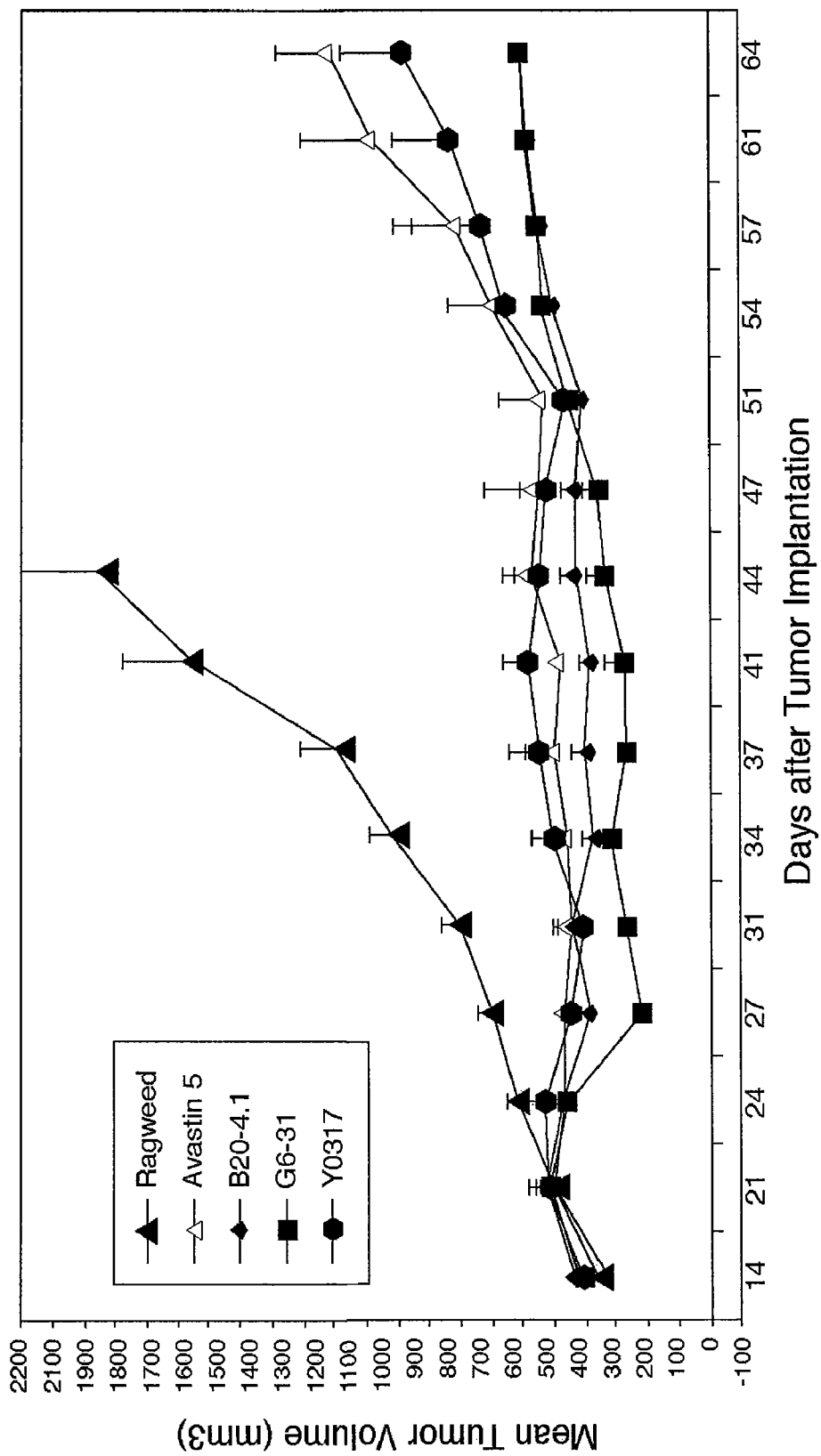
FIG. 2E shows tumor growth curves of Calu-6 tumors treated after tumor-volumes reached 500 mm$^3$ (regression experiment) with either control, B20-4.1, G6-31, bevacizumab or Y0317 Mab (5 mg/kg, IP, twice weekly). B20-4.1 and G6-31 treated tumors were significantly smaller than bevacizumab treated tumors
Figure 2H:
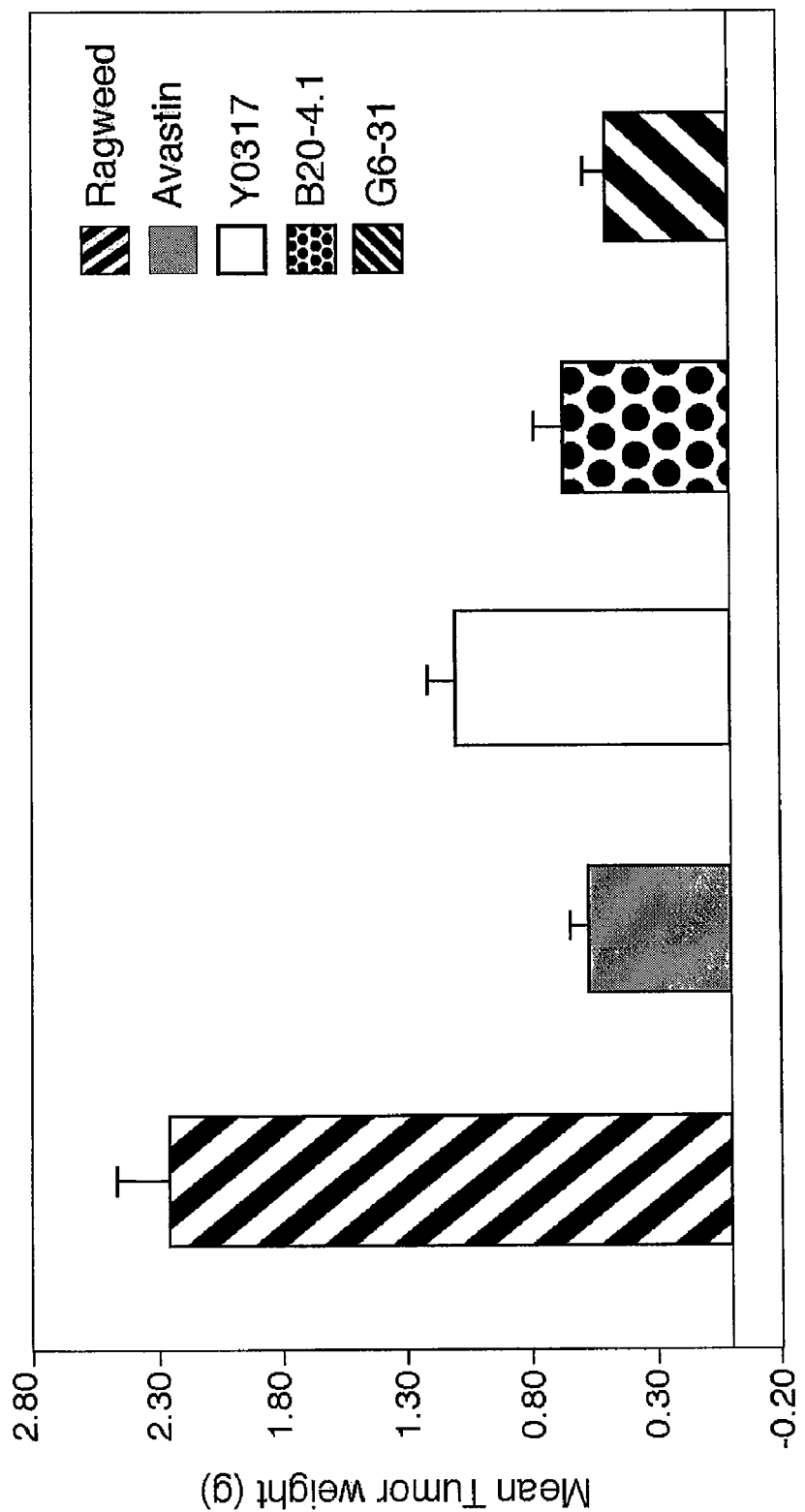
FIG. 2H shows teiminal tumor weights of HM7 tumors on day 58 of treatment with various anti-VEGF Mabs.

Immuno-compromised RAG2 ko; hum-X VEGF ki double homozygous mice were generated by mating hum-X VEGF het females (B6.129) to Rag2.ko males {B6 (H2b) (Taconic, #RAGN12-M) }. Double heterozygous animals were interbred to produce double homozygous hum-X VEGF.ki; Rag2.ko animals. The strain is maintained as double mutant breeding sets. These were used to assess the potency and efficacy of bevacizumab, hY0317, hG6-31 and hB20-4.1 to inhibit growth of Calu-6 (lung carcinoma), HT29 or HM7 (colorectal carcinoma) tumor xenografts. As shown in FIG. 2, when given at the dose of 5 mg/kg twice weekly, bevacizumab and hY0317 interfered to similar extents with growth of human Calu-6 lung carcinoma tumors, despite significant differences in their relative binding affinities for VEGF-A. Similarly, B20-4.1 and G6-31 were equally efficacious in inhibiting growth of Calu-6 lung carcinoma cells (FIGS. 2A, 2B). A similar response was observed when antibodies were tested in HM7 tumors (FIGS. 2C, 2D). In the majority of tumor intervention experiments, when anti-VEGF antibodies were administered 3 days after tumor cell implantation, we noted a trend towards improved tumor growth inhibition by B20-4.1 and G6-31 Mabs relative to bevacizumab or Y0317 (e.g. FIG. 2 A-D). These findings suggest that increased binding affinity alone is insufficient to improve efficacy in tumor xenograft studies, and that the epitope recognized by anti-VEGF-A antibodies might play a role in determining the therapeutic efficacy. Administration of lower doses (0.5 mg/kg twice weekly) did not show a clear advantage linked to higher affinity and in vitro potency. In fact, at this dose the highest affinity Mab Y0317 paradoxically resulted in the lowest degree of tumor growth inhibition among other Mabs tested.

Finally, we tested the ability of anti-VEGF-A antibodies to induce regression of already established tumors. Human HT29 (colorectal carcinoma) and Calu-6 (lung carcinoma) cells were obtained from the American Type Culture Collection. The human colorectal carcinoma HM-7 cell line is a derivative of LS 174T (46). Tumor cells were maintained in culture with DMEM/F12 medium, supplemented with 10% FBS. Cells were grown at 37° C. in 5% $CO_2$ until confluent, harvested, and resuspended in sterile MatrigelTM at $25 \times 10^6$ cells per ml. Xenografts were established in 6- to 8-week-old female Beige Nude XID mice by dorsal flank s.c. injection of $5 \times 10^6$ cells/mouse and allowed to grow. When tumors reached volume of ~400 mm³ (regression) or 150-200 mm³ (intervention), a cohort was randomly selected (n=10) as day-0 controls. The remaining mice were divided into groups of ten mice and antibodies were administered i.p. at the same dose for each group. Tumor sizes and weights were measured as described previously (Gerber et al. Cancer Res. 60:6253-58 (2000)). For this purpose, we administered bevacizumab, hY0317, hB20-4.1 and hG6-31 to mice implanted with Calu-6 (FIG. 2E, F) or HT29 tumors (FIG. 2G, H) when tumor reached an average size of ~400 mm³. All antibodies potently suppressed tumor growth, indicating similar efficacy in the regression setting. However, similar to the observations made from intervention experiments, there was a trend towards increased efficacy of Mabs B20-4.1 and G6-31.

Example 4

This example demonstrates the use of hum-X VEGF mice for testing the safety of VEGF directed therapy.

We treated hum-X VEGF-ki mice when reaching 3, 6 or 9 months of age for prolonged periods of time. 8 to 9 month-old hum-X VEGF-ki mice were treated twice weekly, IP, with 10 mg/kg of antibody for the duration of 90 days. Alternatively, 5 mg/kg, IP, once weekly was administered. Body weights were assessed weekly, serum was harvested via retro-orbital bleeding and submitted for pharmacokinetic and blood chemistry analysis. Mice were euthanized when changes in body weights exceeded 20% and/or ascites formation was prominent.

Tumor tissues were fixed in 10% neutral buffered formalin for 12-16 h prior to paraffin embedding. Histologic sections 4-5 microns thick were stained with hematoxylin and eosin. Murine VEGF-A was detected using 0.5 micrograms/ml goat polyclonal antibody from R&D Systems (AF-493-NA); rehydrated paraffin-embedded tissues were treated with Target retrieval solution (DAKO, S 1700) at 99 degrees C. for 20 minutes, followed by 20 minutes at room temperature. Primary antibody was detected with biotin-conjugated rabbit anti-goat, avidin-biotin complex (Vectastain® Elite ABC, Vector Labs) and metal-enhanced diaminobenzidine (Pierce). Complement C3 was detected by direct immunofluorescence on frozen sections using FITC-conjugated anti-complement F(ab')2 (Cappel Labs). Anti-VEGF monoclonal antibodies were detected by direct immunofluorescnce using FITC-conjugated rabbit anti-human Fc (Jackson Immunoresearch). Methacrylate-embedded 1-micron thick sections were stained with toluidine blue or Jones silver stain for basement membrane. Ultrathin sections were stained with uranyl acetate/lead citrate and examined on a Philips CM 12 transmission electron microscope. Antibodies were administered to hum-X VEGF ki mice at low (5 mg/kg, IP, once weekly) or high doses (10mg/kg, IP, twice weekly) for 12 consecutive weeks. Treatment with higher affinity Mabs was frequently associated with the formation of ascites, which was dose-dependent. The effect was seen infrequently at doses of <5 mg/kg weekly but wasfrequent at higher doses. In contrast, administration of the lower affinity A4.6.1 or mB20-4.1 Mabs did not result in ascites formation. Serum chemistry and urine analysis on days 84-90 (A4.6.1, B20-4.1, G6-31) or when animals became moribund (Y0317) revealed increased ALT, AST and BUN levels, consistent with liver and kidney injury.

Histological analysis of all major organs identified no significant changes in heart, spleen, pancreas and lung in any treatment group. However, there were subtle changes in the liver and more significant changes in kidney, both of which were most prominent in mice treated with higher affinity anti-VEGF Mabs for long durations. In animals treated with anti-VEGF antibodies, H&E-stained liver samples showed increased numbers of mononuclear cells adherent to central veins, while portal veins appeared normal. The adherent cells were F4/80- and MAC-2-positive, consistent with macrophages of Kupffer cells; some contained phagocytosed red blood cells. Increased VEGF-A staining was present in sinusoidal endothelial cells. By direct immunofluorescence, no detectable anti-VEGF antibody or complement C3 deposition was noted in frozen samples of the same liver samples.

Kidneys of animals treated for extended intervals with anti-VEGF showed glomeruloslerosis, which was generally more severe in animals treated with high-affinity anti-VEGF antibodies. Glomeruli in the most affected animals showed severe diffuse global sclerosis. Immunostaining for murine VEGF-A showed marked differences between control and anti-VEGF treated animals: control glomeruli showed moderate signal in podocyte cell bodies, with little detectable signal in capillary loops. In contrast, anti-VEGF-treated glomeruli showed increased mesangial and capillary loop staining, roughly in proportion to the affinity of the respective antibodies. In addition, juxtamedullary glomeruli showed more intense and widespread staining than the corresponding peripheral cortical glomeruli in the same animal. Anti-human Fc direct immunofluorescence showed increased anti-VEGF deposition (diffuse, finely granular pattern) in glomeruli, which was more prominent with antibodies of increased affinity. Similarly, complement C3 staining was increasingly prominent in animals treated with higher affinity anti-VEGF antibodies. MAC-2 immunohistochemistry showed no significant infiltration of monocyte/ macrophages in glomeruli from anti-VEGF-treated animals. Toluidine-blue and silver staining of methacrylate-embedded 1 micron sections confirmed the observations from paraffin and frozen sections, showing increased mesangial cellularity, and widening of mesangial matrix and capillary loops with material that stained differently from native basement membrane. Electron microscopic examination showed focal subendothelial deposits in capillary loops, endothelial swelling, increased mesangial matrix and mesangial cell number. In contrast, podocyte foot processes were relatively spared, though focal foot process fusion was evident in the more severely affected glomeruli. Together, these observations are most consistent with the presence of VEGF-anti-VEGF complexes deposited in the glomeruli.

All publications (including patents and patent applications) cited herein are hereby incorporated in their entirety by reference in their entireties for all purposes.

What is claimed is:

1. A transgenic mouse comprising in its genome a heterologous nucleic acid encoding the humanized VEGF protein (hum-X VEGF) set forth in SEQ ID NO:12 operably linked to a promoter, wherein said transgenic mouse comprises a homozygous disruption of its endogenous mouse VEGF gene, does not express the endogenous mouse VEGF protein, and expresses the hum-X VEGF set forth in SEQ ID NO:12.

2. The transgenic mouse of claim 1, wherein said transgenic mouse further comprises in its genome a homozygous disruption of the RAG2 gene, wherein said transgenic mouse does not express RAG2 and said transgenic mouse is immuno-compromized.

3. A cell or tissue obtained from the transgenic mouse of claim 1.

4. An isolated nucleic acid encoding hum-X VEGF as set forth in SEQ ID NO: 12.

* * * * *